United States Patent
Zhang et al.

[19]

[11] Patent Number: 6,111,416
[45] Date of Patent: Aug. 29, 2000

[54] ELECTRO-OPTICAL AND MAGNETO-OPTICAL SENSING APPARATUS AND METHOD FOR CHARACTERIZING FREE-SPACE ELECTROMAGNETIC RADIATION

[75] Inventors: Xi-Cheng Zhang, Latham; Jenifer Ann Riordan, Massapequa; Feng-Guo Sun, Troy, all of N.Y.

[73] Assignee: Rensselaer Polytechnic Institute, Troy, N.Y.

[21] Appl. No.: 08/920,561

[22] Filed: Aug. 29, 1997

Related U.S. Application Data

[63] Continuation of application No. 08/859,478, May 20, 1997, abandoned, which is a continuation-in-part of application No. 08/739,099, Oct. 25, 1996, Pat. No. 5,952,818.
[60] Provisional application No. 60/018,844, May 31, 1996.
[51] Int. Cl.$^7$ ................................................. G01R 31/308
[52] U.S. Cl. ............................................. 324/753; 324/96
[58] Field of Search ............................ 324/96, 753, 750, 324/244.1, 117 R; 250/227.21, 225; 359/280–283, 257; 356/365, 368

[56] References Cited

U.S. PATENT DOCUMENTS

| | | | |
|---|---|---|---|
| 3,675,125 | 7/1972 | Jaecklin | 324/96 |
| 3,769,584 | 10/1973 | Iten et al. | 324/96 |
| 3,927,945 | 12/1975 | Bates | 356/106 |
| 4,070,621 | 1/1978 | Bassen et al. | 324/96 |
| 4,595,876 | 6/1986 | Kuhara et al. | 324/96 |
| 4,618,819 | 10/1986 | Mourou et al. | 324/77 K |
| 4,873,485 | 10/1989 | Williamson | 324/96 |
| 4,891,581 | 1/1990 | Takiguchi | 324/96 |
| 4,896,103 | 1/1990 | Shimanuki et al. | 324/96 |
| 4,910,458 | 3/1990 | Forsyth et al. | 324/158 R |
| 4,928,058 | 5/1990 | Williamson | 324/96 |
| 5,006,789 | 4/1991 | Williamson | 324/96 |
| 5,134,361 | 7/1992 | Pillow | 324/96 |
| 5,406,194 | 4/1995 | Dykaar et al. | 324/96 |

OTHER PUBLICATIONS

Wu et al., "Free–Space Electro–Optic Sampling of Terhertz Beams," Appl. Phys. Lett., Vo. 67, No. 24, pp. 1–3, Dec. 1995.

Jespen et al., "Detection of High Power THz Pulses by Phase Retardation in an Electro–Optic Crystal," International Symposium on Ultra–Fast Processes In Spectroscopy, Trieste, Italy Oct. 30–Nov. 3, 1995, pp. 1–7.

Hu et al., "Imaging with Terahertz Waves," Optic Letters, vol. 20, No. 16, pp. 1716–1719, May 1995.

A Lauren Publication Biophotonics, "Bell Labs"T–rays' Provide Unique Images With a Variety of Potential Applications," Biophotonics International, pp. 58–59, Jul./Aug. 1995.

Nahata et al., "Coherent Detection of Freely Propagating Terhertz Radiation by Electro–Optic Sampling," Appl. Phys. Lett., vol. 68, No. 2, pp. 150–152, Jan. 1996.

(List continued on next page.)

*Primary Examiner*—Vinh P. Nguyen
*Assistant Examiner*—Russell M. Kobert
*Attorney, Agent, or Firm*—Heslin & Rothenberg, P.C.

[57] ABSTRACT

Apparatus and methods for characterizing free-space electromagnetic energy, and in particular, apparatus/method suitable for real-time two-dimensional far-infrared imaging applications are presented. The sensing technique is based on a non-linear coupling between a low-frequency electric (or magnetic) field and a laser beam in an electro-optic (or magnetic-optic) crystal. In addition to a practical counter-propagating sensing technique, a co-linear approach is described which provides longer radiated field-optical beam interaction length, thereby making imaging applications practical.

20 Claims, 21 Drawing Sheets

OTHER PUBLICATIONS

Nuss, Martin C., "Chemistry is Right for T–Ray Imaging," IEEE Circuits and Devices, pp. 25–29, Mar. 1996.

Hu, B.B., Zhang, X.–C., Auston, D.H. and Smith, P.R., "Free–Space Radiation From Electro–Optic Crystals", 1990 American Institute of Physics, Appl Phys, Lett. 56(6), Feb. 5, 1990 (pp. 506–508).

Green, B.I., Federici, J.F., Dykaar, D.R., Jones, R.R. and Bucksbaum, P.H., "Interferometric Characterization of 160 fs Far–Infrared Light Pulses", 1991 American Institute of Physics, Appl. Phys. Lett. 59(8), Aug. 19, 1991 (pp. 893–895).

Wu, Q. and Zhang, X.–C., "Ultrafast Electro–Optic Field Sensors", 1996 American Institute of Physics, Appl. Phys. Lett. 698(12), Mar. 18, 1996 (pp. 1604–1606).

Wu, Q., Litz, M. and Zhang, X.–C., "Broadband Detection Capability of ZnTe Electro–Optic Field Detectors", 1996 American Institute of Physics, Appl. Phys. Lett. 68(21), May 20, 1996 (2924–2926).

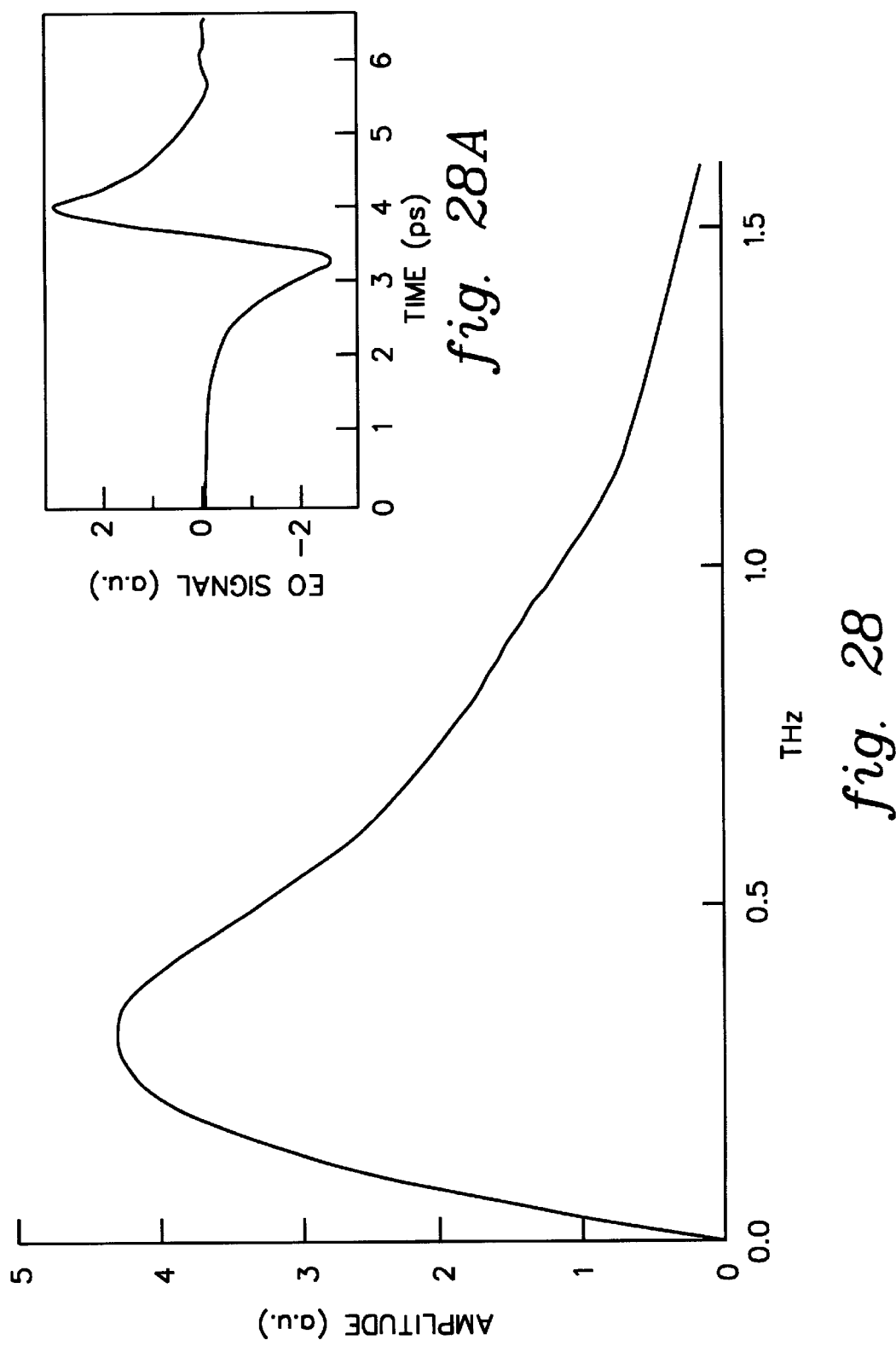

ELECTRO-OPTICAL AND MAGNETO-OPTICAL SENSING APPARATUS AND METHOD FOR CHARACTERIZING FREE-SPACE ELECTROMAGNETIC RADIATION

RELATED APPLICATION INFORMATION

This application comprises a continuation of U.S. application Ser. No. 08/859,478, filed May 20, 1997, now abandoned, which is a continuation-in-part of U.S. application Ser. No. 08/739,099, filed Oct. 25, 1996, now U.S. Pat. No. 5,952,818 which itself comprises a regular U.S. application claiming the benefit of U.S. Provisional Application No. 60/018,844, filed May 31, 1996. These Provisional and regular Applications are hereby incorporated by reference herein in their entirety.

TECHNICAL FIELD

The present invention relates to apparatus and methods for coherently characterizing a free-space electromagnetic field, and in particular, to apparatus and methods suitable for real-time two-dimensional far-infrared imaging applications.

BACKGROUND ART

In the ultrafast electronics and optoelectronics communities, especially in the sub-field of applied terahertz beams, the detection of freely propagating picosecond microwave and millimeter-wave signals is primarily being carried out via photoconductive antennas and far-infrared interferometric techniques. For example, reference an article by Hu and Nuss entitled "Imaging With Terahertz Waves," Optics Letters, Vol. 20, No. 16 (August 1995).

Photoconductive antennas have good detection responsivity, and their signal-to-noise ratios are typically far better than liquid helium cooled bolometers. Further, the detection bandwidth of a photoconducting antenna with a short dipole length can exceed 5 THz. However, the limitation of these antenna-based detectors is the resonant behavior of their Hertzian dipole structure. This type of structure has a resonant wavelength at twice the dipole length and therefore the signal waveform, which includes the resonant detector response function, is not a simple cross-correlation of the incoming terahertz and optical gating pulses. Even if the temporal resolution of photoconductive antennas, which is limited by the finite lifetime of photo carriers in the optical gate and antenna geometry, is reduced below 100 fs, the measured signal will still not provide an accurate representation of the actual terahertz waveform.

In comparison, although far-infrared interferometric techniques provide an autocorrelation of terahertz pulses, important phase information is still lost. In most field-matter interconnection applications, knowledge of the entire terahertz waveform, including both the amplitude and phase, is crucial. Thus, to support a variety of advanced scientific and technological applications, there continues to exist a need for the development of more suitable sensing devices.

An electro-optic sampler is especially suitable for measurement of picosecond transient signals. Such samplers have been applied in the art for "local field" measurement, including measurement of signals produced by photodiodes, integrated circuits and other fast devices which either have an electrical stimulus and electrical output or an optical stimulus and an electrical output. These "local field" electro-optic sampling systems, such as described in U.S. Pat. Nos. 4,618,819, 4,910,458 and 5,406,194, typically utilize Pockels effect. A Pockels cell comprises what is referred to as an electro-optic crystal which has the property of variable birefringence as a function of electrical field applied thereto.

The electro-optic crystal is utilized in the "local field" context as follows: an optical pulse train is provided from a source and split into two different paths, a sampling beam and a stimulus beam. One such source is a visible wavelength picosecond laser. Optical pulses in the first path trigger generation of the electrical signal to be measured. This electrical signal is coupled to be accessible to the electro-optic crystal, through which optical sampling pulses of the second path are propagated. The crystal is in an optical path between first and second crossed polarizers. The field-induced birefringence varies the polarization of the sampling beam. The sampling beam intensity after polarization analysis is measured by a detector, for example, a slow photodiode, one which does not have to resolve individual pulses.

The detector output is provided to utilization means. Electrical output from the detector as well as electrical output indicative of modulation of pulses in the stimulus beam are first coupled to a lock-in amplifier which yields a dc output proportional to the amplitude of the sampled electrical signal in phase with the modulation of the stimulus beam. A display can be generated by plotting the output of the lock-in amplifier during successive pulse periods against the output of a variable delay line synchronized with the display device. The basic theory of electro-optic sampling is explained in Vladmanis and Mourou, "Electro-Optic Sampling: Testing Picosecond Electronics," Laser Focus/Electro-Optics, p. 84, February, 1986, and Vladmanis, Mourou and Gabel, IEEE Journal of Quantum Electronics, Vol. QE-19, 4, p. 664, April 1983. An effective electro-optic sampler for measuring signals having temporal components on the order of picosecond is disclosed in U.S. Pat. No. 4,446,425 issued to Vladmanis and Mourou.

In the most common implementation of electro-optic sampling, the electro-optic sampler is embodied in a test fixture composed of three parts. These are a metal or ceramic carrier, a photoconductive switch and an electro-optic crystal. The carrier provides mechanical support for active devices. The active devices include the electro-optic crystal itself, the photoconductive switch and the device-under-test. Electrical connections are made from the device-under-test to the waveguides in the switch and on the crystal as well as to a bias network typically with gold wire bonds.

In the operational mode, the photoconductive switch has appropriate bias supplied thereto. When it is stimulated with the stimulating beam described above, an electrical pulse with picosecond rise time is launched down the waveguide. This is the stimulus signal which stimulates or turns on the device-under-test. The device-under-test produces an electrical output pulse which is then launched down the waveguide on the crystal surface where its electrical field effects the birefringence of the electro-optic crystal and is sampled by the second train of optical pulses.

Although achieving good performance for quantifying "local field" characteristics, electro-optic sampling as known in the art and summarized herein, has heretofore been unworkable for free-space radiation characterization. This is principally because of the different natures of local field and free-space electromagnetic waves.

Thus, there exists a need in the art for a practical electro-optic sampling apparatus and method capable of sampling free-space radiation, and particularly to one which is suitable for real-time two-dimensional far-infrared imaging applications.

DISCLOSURE OF INVENTION

Briefly summarized, the invention comprises in one aspect a magneto-optical sensor for characterizing a free-space magnetic field. The sensor includes a magneto-optic crystal positionable so that the free-space magnetic field passes therethrough and changes an index of refraction of the crystal. An optical probe signal is generated and impinges upon the magneto-optic crystal simultaneous with the free-space magnetic field passing therethrough such that the optical probe signal collects information representative of the magnetic field passing through the crystal. A sensing means is provided for detecting the optical probe signal after passing through the crystal to determine ellipticity modulation of the optical probe signal. Processing means then characterize the free-space magnetic energy by evaluating this ellipticity modulation of the optical probe signal.

Although described herein principally as electro-optical sensing for characterizing a free-space electromagnetic field, it should be understood that the invention also encompasses the above-summarized magneto-optic sensing techniques for characterizing free-space magnetic fields.

Numerous advantages are inherent in the novel apparatus and methods presented herein in comparison with any previous sensing technology. Preliminary data with zinc telluride (ZnTe) probes indicates diffraction-limited spatial resolution, femtosecond temporal resolution (177-fs pulse duration), and a 5 THz bandwidth are attainable. The simplicity of the detection geometry, the capability of optical parallel processing, and the excellent signal-to-noise ratio attainable ($\geq 10,000$) make an apparatus/method in accordance with the present invention suitable for real-time two-dimensional subpicosecond far-infrared imaging applications.

The field sensor area can be scaled with the area of the crystal, therefore the technique is inherently capable of parallel optical processing. The approach is compatible with CCD and DSP technologies. The field sensor device avoids previous limitations inherent in the existing art by the resonant structure of photoconductive dipole antennas. A flat frequency response from dc to the first phono resonance frequency (typically several terahertz) is attainable, thereby producing an ultrawide-band frequency response.

A sensor in accordance with the invention can be used with large temperature variations, for example, -250° C. to +200° C. The electromagnetic field sensor is easy to set up, and no focusing elements are required. Virtually no perturbation of the electromagnetic field is caused by the sensing device. The sensor has a 100,000,000 power dynamical range. No electrode or wiring element is required and the device can be used for terahertz field imaging.

The detector area is the area of the sensor crystal, which may be as large as 4 inches if GaAs sensor crystal is used, or as small as 50 $\mu$m for a single beam application. Again, the larger size is suitable for far-infrared imaging. The electro-optic sensor plate measures both amplitude and phase of freely propagating electromagnetic waves within the bandwidth from dc to several terahertz.

The sensitivity of the field sensor device scales with the electro-optic co-efficient, and the interaction length between the optical beam and the electromagnetic beam. The field sensor does not require intense probe beam power, and by using conventional photodiode detectors for the optical probe beam, the probe beam power can be varied between 10 nW to 10 mW, which is significantly lower than any pre-existing optoelectronic technique. Finally, organic materials may be employed for the sensor head to increase detection sensitivity.

BRIEF DESCRIPTION OF THE DRAWINGS

The subject matter which is regarded as the present invention is particularly pointed out and distinctly claimed in the concluding portion of the specification. The invention, however, both as to organization and methods of practice, together with further objects and advantages thereof, may best be understood by reference to the following detailed description taken in conjunction with the accompanying drawings in which:

FIG. 28 is a plot of the frequency spectrum of the temporal waveform of FIG. 28a measured by one pixel of the CCD of FIG. 27;

FIG. 28a is the temporal signal recorded from a single CCD pixel of FIG. 27;

BEST MODE FOR CARRYING OUT THE INVENTION

Terahertz imaging is a novel technology that operates in the submillimeter-wave region of the electromagnetic spectrum. Recent advances in high-speed optoelectronic and femtosecond laser technology facilitate generation and detection of short bursts of terahertz radiation, which has been proven to be extremely useful for spectroscopic measurements in the submillimeter-wave range. Terahertz imaging combines these spectroscopic measurements with real-time imaging and advanced signal processing and recognition, so that each pixel element of the image contains spectroscopic information about the object. In many cases, the spectroscopic information provides significant clues about the chemical composition of the object of interest. Terahertz radiation is described in greater detail in an article by M. Nuss entitled "Chemistry is Right for T-Ray Imaging," Circuits & Devices, IEEE (March, 1996.)

Generally stated, described herein are apparatus and method for free-space electro-optic characterization of propagating terahertz beams. Unlike pre-existing approaches, free-space electro-optic sampling in accordance with the present invention can provide usable knowledge of an entire terahertz waveform, including both amplitude and phase. As used herein, the term "free space" means that the electro-optic sensor is placed remote from the microwave or electric field emitter, i.e., is placed in "far field." Distances as far as 1 meter have been experimentally verified. The sensing technique is based on a non-linear coupling between a low-frequency electric field (terahertz pulse) and a laser beam (optical pulse) in an electro-optic crystal, such as a zinc telluride (ZnTe) crystal. Modulating the crystal's birefringence by applying the polarized electric field thereto will modulate the polarization of ellipticity of the optical probe beam passing through the crystal. This ellipticity modulation of the optical beam is then polarization-analyzed to provide information on both the amplitude and phase of the applied electric field.

Preliminary data with ZnTe probes indicates subwavelength spatial resolution, femtosecond temporal resolution (177-fs pulse duration), and a 5 THz bandwidth are obtainable. Perhaps most significant, the simplicity of the detection geometry, the capability of optical parallel processing, and the excellent signal-to-noise ratio attainable ($\geq 100,000$) make an apparatus/method in accordance with this invention suitable for real-time two-dimensional subpicosecond far-infrared imaging applications.

Figure 1:
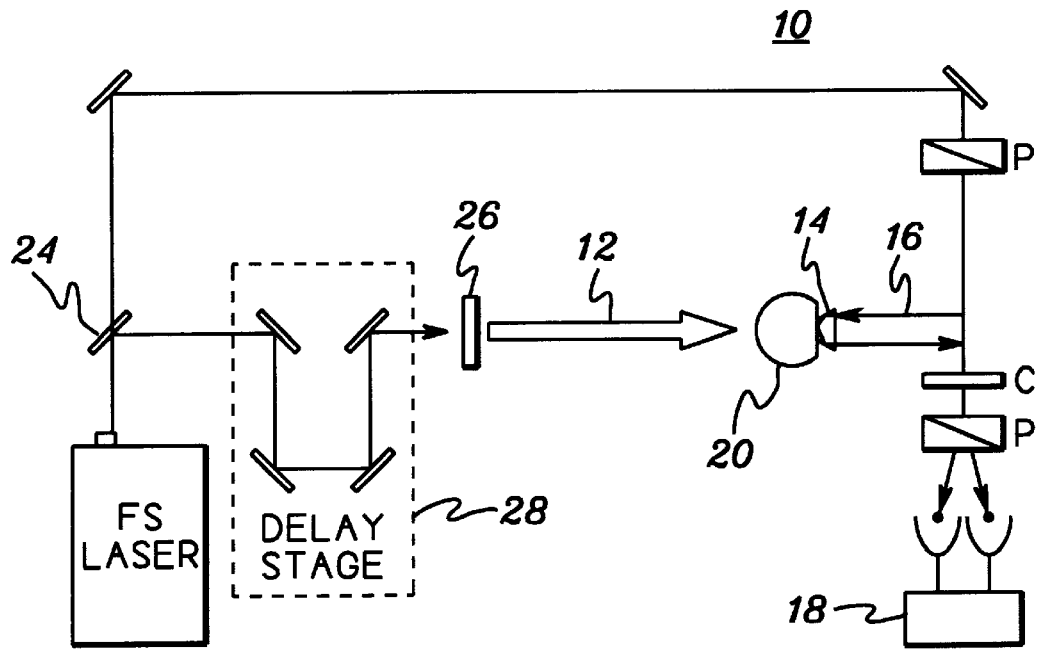
FIG. 1 is a diagram of one embodiment of an electro-optic sampling apparatus in accordance with the present invention for sampling free-space radiation wherein the optical probe pulse is counter-propagating relative to the free-space radiation.

Referring now to the drawings, wherein the same reference numbers are used throughout multiple figures to designate the same or similar components, one embodiment of free-space electro-optic sampling in accordance with the present invention is depicted in FIG. 1. This detection geometry comprises a counter-propagating approach wherein the optical probe signal is incident on the electro-optic crystal in a direction counter to the direction of the electromagnetic field passing through the crystal. The crystal is configured to refract the optical pulse signal such that the signal has a velocity component in the same direction as the electromagnetic energy passing through the crystal.

Operationally, sensing of the electromagnetic field operates as follows. An electromagnetic field signal is applied to the electro-optic crystal which causes a change in low frequency polarization within the electro-optic crystal. This change in low frequency polarization causes an index of refraction change within the crystal. The change in index of refraction is sensed by the optical probe signal illuminated on the electro-optic crystal. A polarization analyzer converts the light polarization change of the optic probe signal into a light intensity change. Finally, this light intensity change is analyzed. The change is known by one skilled in the art to be proportional to, and characteristic of, the electromagnetic field signal. This signal analysis is analogous to that being done today in the "local field" context.

In FIG. 1, when the pulsed electromagnetic radiation (THz pulse) 12 illuminates the electro-optic crystal 14, the index of refraction is modulated via the Pockels effect. A femtosecond optical pulse 16 probes the field-induced change in the index of refraction by passing through the crystal. To convert the field-induced ellipticity modulation into an intensity modulation, the probe pulse is analyzed by a compensator (C) and polarizer (P), then detected by the photodetector. To improve detection efficiency, the THz beam is focused by a high resistivity silicon lens 20, thereby significantly increasing the transient bias of the sensor crystal. Further, an optical chopper can be used to modulate the laser pump beam and a lock-in amplifier may be employed for noise reduction. These are not essential, and their use depends upon the implementation. For example, if imaging with a parallel optical probe input, then an optical chopper and lock-in amplifier would not be used.

The sampling apparatus, generally denoted 10, comprises a setup useful in discussing concepts in accordance with the present invention. As a detailed example, a cw $Ar^+$ laser pumped, mode-locked Ti:sapphire laser 22 (coherent MIRA) provides 150 fs optical pulses at 820 nm with a 76 MHz repetition rate. The laser signal is split 24 to provide a probe pulse 16, and the trigger to an emitter 26 via an appropriate delay stage 28. Emitter 26, again triggered by the femtosecond laser pulses, may comprise a GaAs photoconductive emitter which radiates THz pulses 12. The planar emitter has a 2 mm photoconductive gap between electrodes. The bias field is 1.5 kV/cm and the average optical power on the emitter is 400 mW. Delay stage 28 allows the development of a waveform which controls phase and amplitude information derived in accordance with the present invention. Presented herein is a coherent measuring system which comprises a "direct" or "absolute" measurement, unlike conventional antennas which provide coherent measurement but with their own response function. The present invention is believed to comprise a novel technique which allows direct measurement of both amplitude and phase for determination of field strength. Further, calibration and mapping of field oscillations can occur.

When pulsed electromagnetic radiation, such as terahertz (THz) pulse 12, illuminates electro-optic crystal 14, the index of refraction of the crystal is modulated via Pockels effect. The electro-optic crystal has an optical axis which must be properly oriented for the crystal to be used as a field sensor in a manner known to the "local field" sensing art. To improve detection efficiency, radiation beam 12 is preferably focused onto the crystal using a lens 20, such as a silicon lens. A counter-propagating, femtosecond optical pulse 16 probes the field-induced change in the crystal's index of refraction by reflecting within the crystal, for example, with a focus spot of 10 micrometers. As one embodiment, a 500 micrometer thick $LiTaO_3$ crystal might be employed as the Pockels cell, with its C-axis parallel to the electric field polarization of the incoming radiation. This sensing arrangement satisfies the desired phase-matching condition, which in $LiTaO_3$ requires an angle of 71 degrees between the THz pulse 12 and the optical pulse 16 as shown best in FIG. 2. (Note that an alternative crystal configuration for "counter-propagating" sensor 10 is depicted in FIGS. 17–21 and discussed below.)

Continuing with FIG. 1, to convert the field-induced ellipticity modulation into an intensity modulation, the probe pulse 16 is passed through a compensator (C) and a polarizer (P), before being detected by a photodetector 18, which provides information on both amplitude and phase of the applied electric field, i.e., THz pulse 12. By way of specific example, the compensator (C) may comprise a Berek compensator, Part No. 5540, marketed by New Focus Inc. of Sunnyvale, Calif., while polarizer (P) may comprise a Glen Laser Polarizer, Part No. GLD-M10-850, marketed by Meadowlark Optics of Longmont, Colo. Further, the photodetector 18 may comprise a silicon photodiode, such as Part No. S2386-18K, marketed by Hamamatsu Corp. of Bridgewater, N.J.

By way of further explanation, a quarter-wave plate (compensator (C)) can be used to provide an optical bias to the probe beam which allows the system to be operated linearly. A Wollaston polarizer (WP) is preferably used to convert the induced phase retardation of the probe beam into intensity modulation on two mutually orthogonal linearly polarized beams. Two unbiased photodiodes (Part No. S5533 marketed by Hamamatsu Corp. of Bridgewater, N.J.) are connected in a balanced mode, similar to the Hamamatsu custom balanced photodiode Part No. S1446. These photodiodes are used to detect optical intensity modulation. Note that if the electro-optic sensor is birefringent, then a compensator must be used. However, if the crystal sensor is not birefringent, such as all zinc blend crystals, like GaAs and ZnTe, then a quarter-wave plate can be used in place of the compensator. Also note that if desired, a fiber optic link could be employed to couple the output of the electro-optic sensor to a detection mechanism. This is an option for any of the sampling approaches presented herein.

Again, when a terahertz beam illuminates an electro-optic $LiTaO_3$ crystal with its polarization parallel to the crystal's axis, the index of refraction is modulated via the Pockels effect. A femtosecond optical pulse with its polarization 45° to the crystal's C-axis, probes the field-induced change in the index of refraction.

Figure 3:
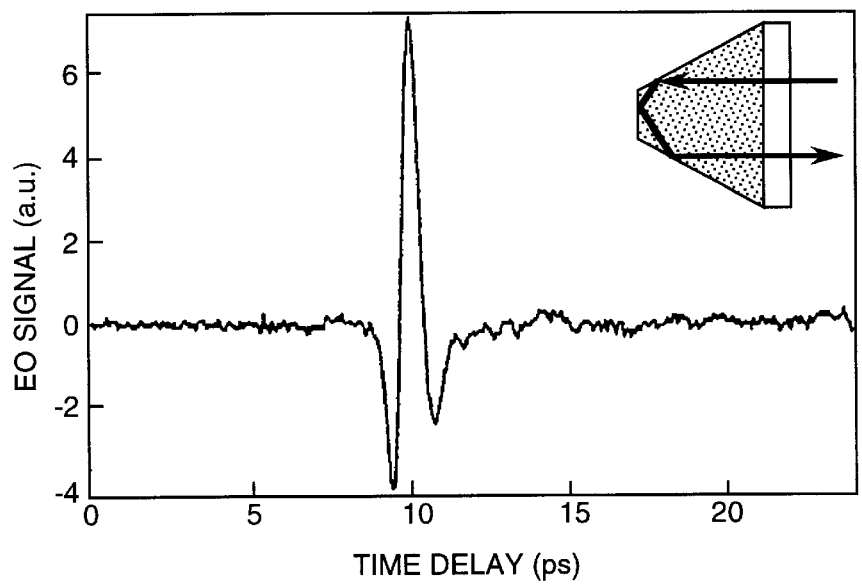
FIG. 3 is a graph of a transient waveform from an unbiased GaAs emitter comprising a plot of electro-optic signal strength versus time delay.

FIG. 3 plots a transient waveform from an unbiased GaAs emitter with a carefully aligned probe beam path to achieve a velocity-matching condition. Due to the good velocity-matching condition, an excellent signal-to-noise ratio is attained. The full-width-at-half-maximum (FWHM) of the main peak is 450 femtoseconds. The field measurement of the electro-optic sensor is purely an electro-optic process, and the system bandwidth is mainly limited by the dispersion of the terahertz signal and the duration of the laser pulse in the crystal, assuming that it is phase-matched. The wide bandwidth obtainable, minimal field perturbation, and true temporal cross-correlation of the free-space electro-optic system are unique characteristics of an implementation in accordance with this invention. It is possible to extract the true terahertz waveform from the cross-correlation signal obtained via free-space electro-optic sampling. This technique eliminates the need for electrical contact with the sensor crystal. Further, real-time terahertz imaging with an electro-optic crystal plate and a CCD camera are scientifically and commercially feasible in accordance with the concepts presented herein.

Figure 2:
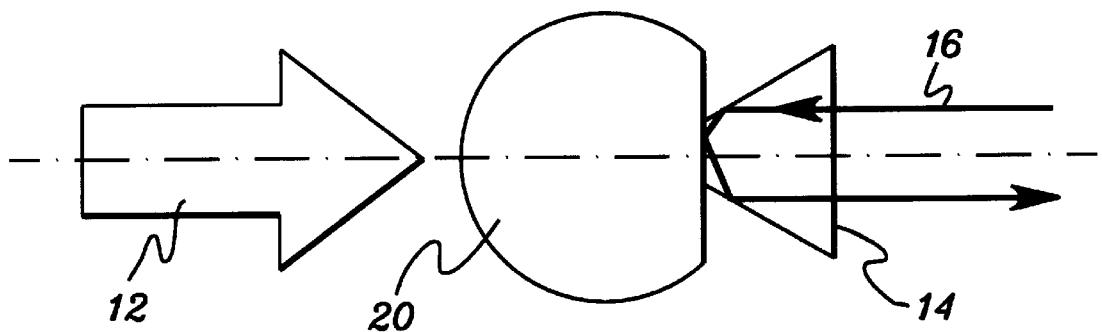
FIG. 2 is an enlarged view of the radiation beam, focusing lens, electro-optic crystal and sampling pulse components of FIG. 1.

In the implementation of FIGS. 1–3, the velocity of the counter-propagating optical beam reflected from the crystal in the projection of the terahertz beam propagation direction matches that of the traveling terahertz field. The interaction length of the optical probe beam and the terahertz beam within the crystal is about 200 micrometers. The nearly velocity-matched condition reduces the walk-off effect, increases the time response, and yields a good signal-to-noise ratio. However, since the terahertz beam and optical beam propagate in opposite directions, if an array of optical beams is used instead of a single beam, as in the case of an imaging application, the configuration could be less than optimal.

Figure 4:
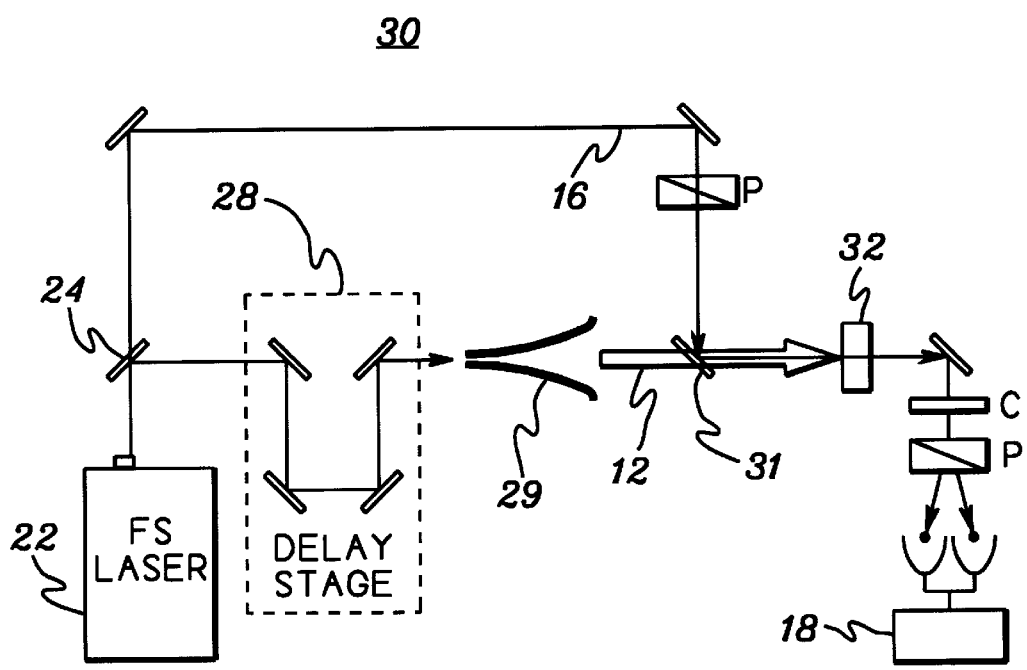
FIG. 4 depicts an alternate embodiment of a free-space sampling apparatus in accordance with the present invention, wherein the optical probe pulse is co-linear with the free-space radiation as the radiation passes through the electro-optic crystal.

To overcome this, FIG. 4 depicts an alternate embodiment wherein the optical and terahertz beams propagate co-linearly within the electro-optic crystal. This sensing apparatus, generally denoted 30, is a unique variation on the counter-propagating approach discussed above. In the embodiment depicted, the electro-optic crystal 32 is assumed to comprise zinc tellurium (ZnTe), which has a comparable electro-optic figure-of-merit ($n^3r/\in$) to that of LiTaO$_3$, but without the limitations associated with intrinsic birefringence, and a reduced sensitivity to thermal fluctuations.

Advantageously, this co-linear propagation embodiment provides a long interaction length between the optical probe beam and the electromagnetic field signal within the crystal, which in a free-space geometry as depicted, provides excellent signal-to-noise ratios. These ratios are much greater than anything attainable using conventional electro-optic sampling geometries. FIG. 4 is similar in set up to FIG. 1 in that a laser 22 provides optical pulses which are split 24 to provide probe pulse 16 and the trigger signal to an emitter, after passing through delay stage 28. The geometry differs from FIG. 1, however, in that a beam splitter 31, such as a 1 inch pellicle beam splitter is employed to align the optical probe beam with a direction that the electromagnetic field 12 is propagating. As an example, the diameters of an unfocused terahertz beam 12 and a pre-focused optical probe beam 16 on the electro-optic crystal 32 may be about 10 mm and 0.2 mm, respectively. This arrangement is similar to that which would be used in a terahertz imaging system, described further below, where the probe beam spot (pixel size) is comparable with the terahertz wavelength.

An 1.5 mm thick ≦110≧ oriented ZnTe crystal is used as the electro-optic sensing head. This orientation yields the largest electro-optic retardation possible in a zinc blend crystal structure, while electrical and optical incidence on the naturally cleaved ≦110≧ surface also produces the best beam quality in the ZnTe. The polarizations of both the optical probe and the terahertz beams are said to be parallel to the ≦110≧ edge of the ZnTe crystal for optimal electro-optic phase modulation. The probe beam is optically biased with a fixed retardation (=BC/2) by a compensator, analyzed by a Wollaston polarizer, and measured by a balanced photodetector as described above. During the measurement, the power ratio of the optical pump/probe beam is about 10,000:1.

Several photoconductively-gated pulsed microwave emitters were tested, including centimeter-sized photoconductive tapped antennas (transient current source), unbiased ≦100≧ GaAs wafers with Brewster angle incidence (transient photoconductive source), and ≦111≧ zinc blend wafers with normal incidence (optical rectification source). These emitters provide microwave pulses with a pulse duration from approximately 150 fs to 65 ps. The shortest microwave pulses are generated from terahertz optical rectification (≦111≧ zinc blend crystal) while the longest pulses are from large-end photoconductive tapped antennas. Note that the temporal resolution of free-space electro-optic sampling can be limited by the laser pulse duration or the optical phono resonance. Resolution as short as 71 femtoseconds has been experimentally established, which is clearly a record for electro-optic sampling.

The first set of emitters tested were photoconductive twin-line center-fed antennas. The antennas have two copper conductors, each resembling an alpine-type horn. A GaAs photoconductor with approximately a 1 mm gap was electrically contacted to a uniform transmission-line section. The length of the open ends of these emitters was on the order of a centimeter, which corresponds to low frequency resonance of several tens of gigahertz. A static bias of 150 V was applied across the photoconductive switch. Typically, the average power of the optical trigger on the emitter was 50 mW. The measured beam radii (1/e points into field) of the pulsed microwave radiation and optical probe beam at the sensor location are approximately 4 centimeters and 0.02 centimeters, respectively. This yields an estimated cross-section-ratio of microwave beam to optical probe beam in the sensor of 40,000:1.

Figure 5:
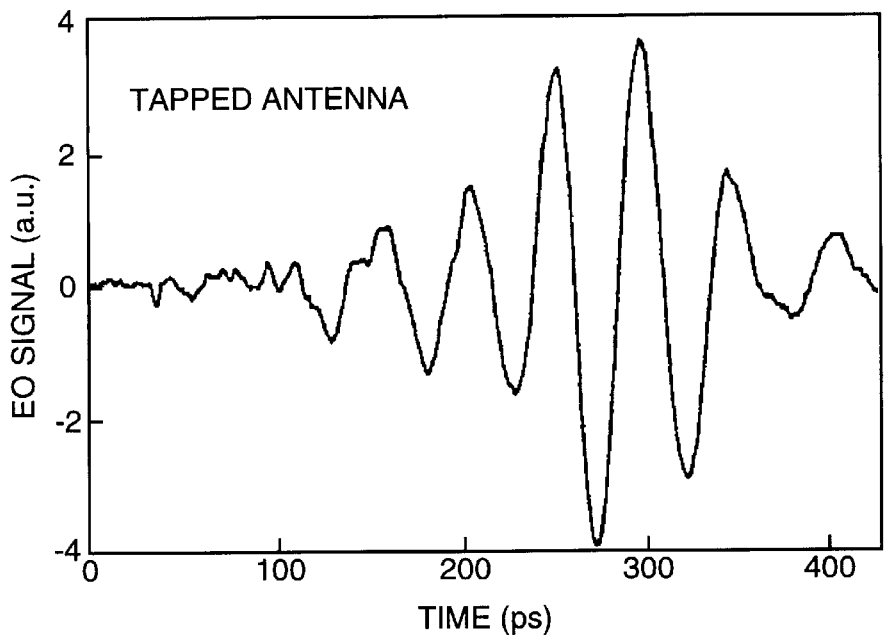
FIG. 5 is a graph of a temporal electro-optic signal from a photoconductive antenna.

FIG. 5 plots a temporal electro-optic signal from one of the photoconductive antennas. The signal lasts for over 1 nanosecond, and only the first 450 picoseconds are presented. The limit results from the time delay stage having a travel distance of 7.5 centimeters, which limits the measurement to 500 ps or correspondingly 2 GHz. With a longer delay stage or electronic scan, the low frequency limit can be brought down to near the laser repetition frequency, which is 82 MHz in one embodiment of the system discussed herein. The small features before the main oscillation are reproducible in the representative scans. The signal-to-noise ratio is better than 100,000:1, even with a 40,000:1 cross-section-ratio of microwave and optical beam.

Figure 6:
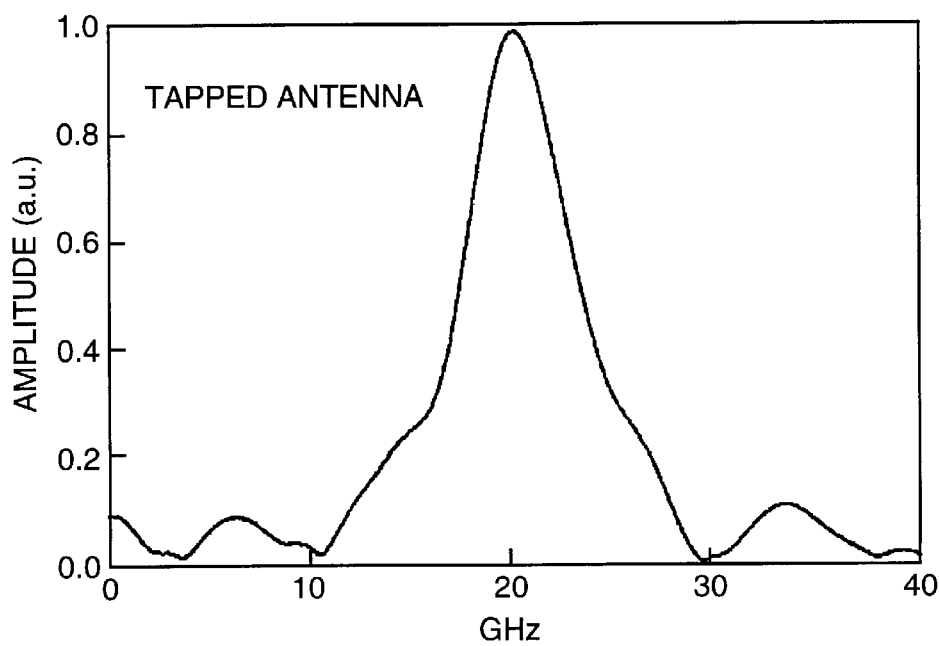
FIG. 6 is a graph of the frequency spectrum of the electro-optic signal from a photoconductive antenna, wherein the spectrum has a center frequency at 20 GHz and a 3 dB bandwidth of 6.3 GHz.

FIG. 6 shows the frequency spectrum with the center frequency at 20 GHz and a 3 dB bandwidth of 6.3 GHz. Increased low frequency components from larger antenna horns have been confirmed by measurements with other antennas.

To restate, demonstrated herein is the broadband detection capability of a co-propagating electro-optic zinc tellurium crystal for the characterization of freely-propagating, pulsed electromagnetic radiation. In a current electro-optic sampling system, the measured high frequency response is the first TO phono resonance of the ZnTe sensor crystal (5.3 THz), and the lowest frequency limit is the laser repetition rate (82 MHz). The upper limit of sensor frequency response is the first transverse optical phono frequency since optical phono in crystals will strongly absorb electromagnetic radiation at phono frequency. It is possible to achieve a higher frequency response by using different electro-optic crystals. For example, InP may be used as a rectified emitter and GaAs as a Pockels crystal since the TO phono frequency of InP and GaAs is 9.12 THz and 8.06 THz, respectively. To approach measurement capabilities below that of a laser repetition rate, a cw laser diode with an electronically controlled time delay scan might be employed rather than the femtosecond laser with mechanical delay-line discussed herein.

Figure 7:
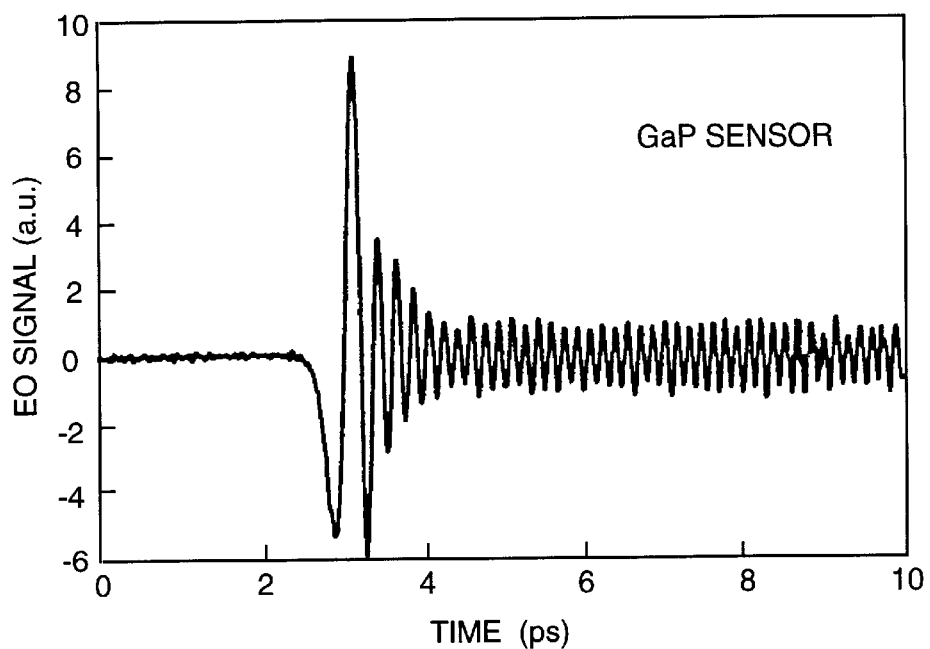
FIG. 7 is graph of a temporal electro-optic signal from optical rectification measured by a GaP sensor.
Figure 8:
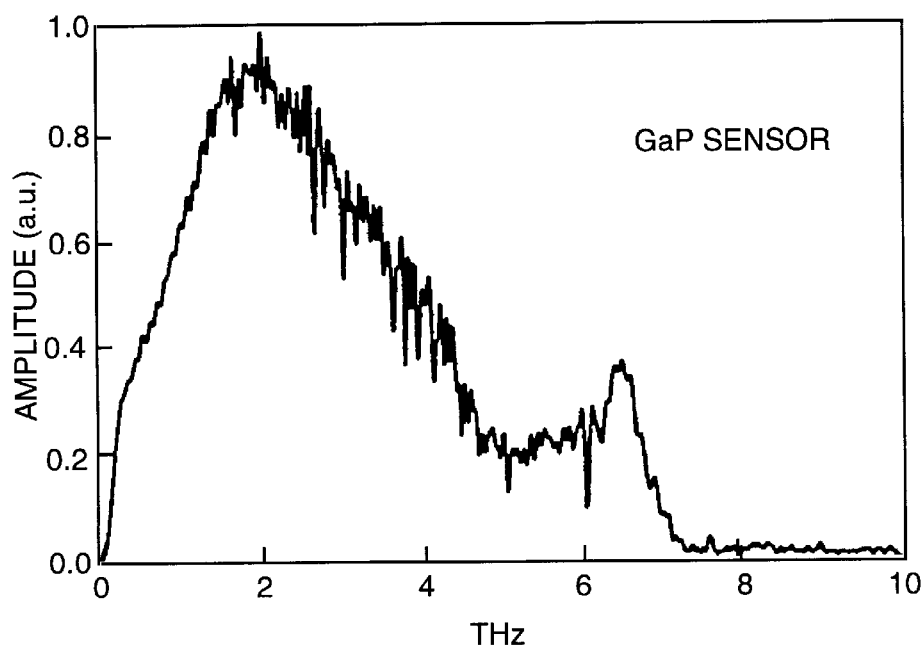
FIG. 8 is a graph of the frequency spectrum of the temporal signal shown in FIG. 7.

Several electro-optic crystals with different phono frequencies have been tested. Results indicate that GaP is a good candidate for higher frequency application. FIG. 7 is a plot of the temporal waveform measured using a ≦111≧ GaP sensor crystal. The laser has a pulse duration of 45 fs, and currently the bandwidth is limited by the GaAs emitter (phono at 8 THz). FIG. 8 is the frequency spectrum and shows the cutoff frequency near 8 THz. Absorption lines of water vapor and other gases are clear. Since GaP has its first phono frequency at 11 THz, by using GaP as both emitter and sensor, a bandwidth greater than 10 THz is expected. The time-resolved 10% to 90% transient in the ring is 50 fs. This is the shortest electrical transient that has been measured coherently.

Figure 9:
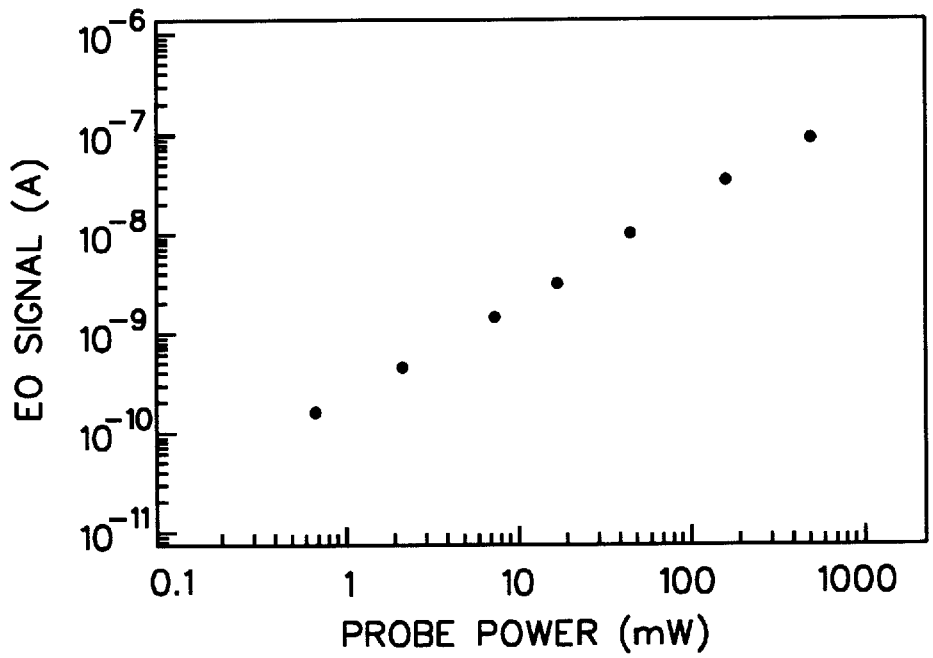
FIG. 9 is a plot of an electro-optic signal (peak-to-peak) versus optical pump power.
Figure 10:
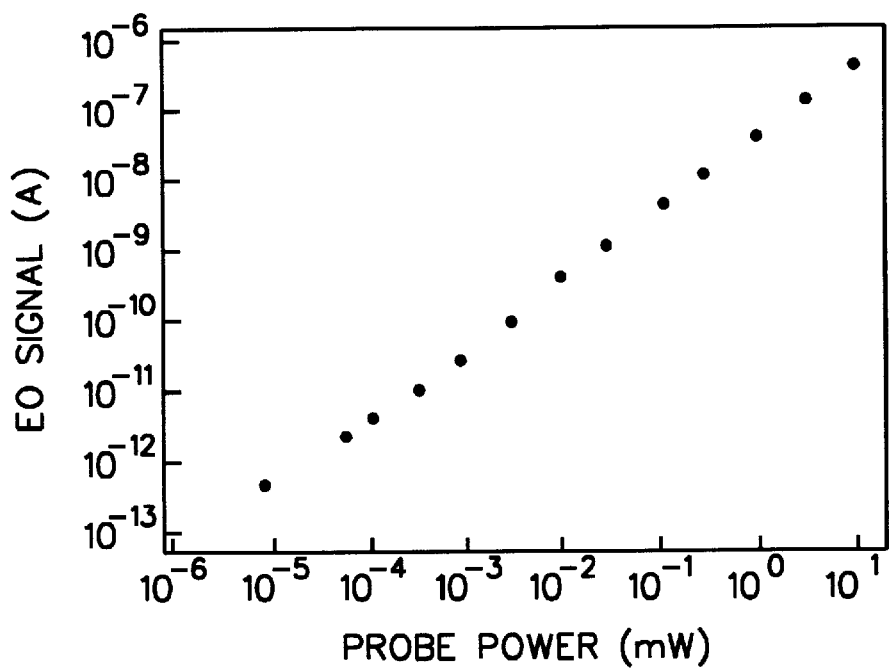
FIG. 10 is a graph of an electro-optical signal (peak-to-peak) versus optical probe power (average)

The dynamic range of free-space electro-optic field sensor for pulsed electromagnetic wave radiation has also been studied. With an optical probe power spanning six decades of linearity and excellent signal-to-noise ratio, it is feasible to convert a far-infrared 2-D image into an optical 2-D image. FIG. 9 is a plot of the electro-optic signal (peak-topeak) versus optical pump power from 0.66 mW to 700 mW. The optical probe power was 2 mW. Since this free-space electro-optic sampling system is operated in the linear range (optically biased at π/2), the measured electro-optic signal is proportional to the THz field, and to the optical excitation power, assuming that the radiated field is proportional to the optical intensity at low power. The slope of the line fit in FIG. 9 is about 200 nA/W. FIG. 10 is a plot of the electro-optic signal (peak-to-peak) versus optical probe power (average) from 8 nW to 9.83 mW. The optical excitation power on the unbiased GaAs emitter was 500 mW. Excellent linearity of electro-optic signal, with the slope of 42 μA/W, is observed over six orders of probe power. The shape of the waveform measured with 8 nW probe power is identical to that measured at 9.8 mW. A signal-to-noise ratio of several thousands remained as the probe power was varied, except for optical probe powers below 50 μW.

Figure 11:
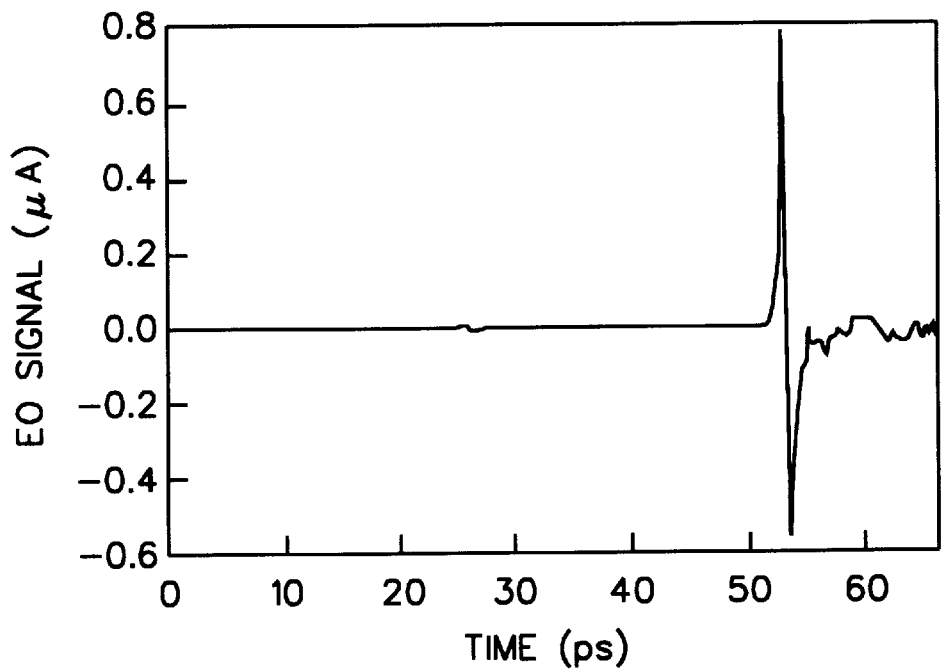
FIG. 11 is a graph of a typical temporal waveform measured using a ZnTe sensor.
Figure 12:
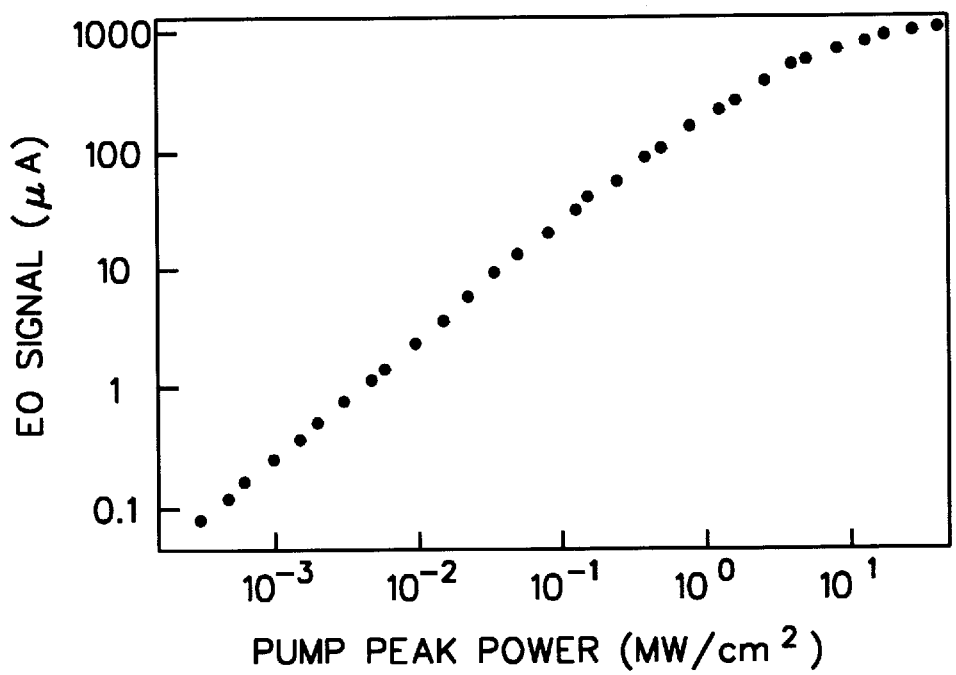
FIG. 12 is a graph of electro-optic signal strength versus optical excitation power.

The linear behavior in both optical pump and probe power at moderate intensity is expected. An amplified laser system was also used as an optical source to generate and detect THz beams. The optical source is a regenerative Ti:Sapphire laser amplifier (Coherent Rega-9000). The pulse duration is about 200 fs, and its repetition rate is 250 kHz. The average optical power is 0.75 W, which corresponds to a pulse energy of 3 μJ. Typically, the average optical excitation power incident on the emitter is about 250 mW, and the optical probe power is about 100 μW. The detection system is similar to that used in a low optical power system. FIG. 11 is a plot of a typical waveform measured using a ZnTe sensor (1.44 mm thick). The signal-to-ratio is greater than 10,000. The small peak before the main signal peak (at 25 ps time location) is due to the sampling effect of the reflected optical probe beam and THz beam in the sensor. In contrast, sampling of the reflected THz beam with optical probe beam starts after the main signal peak. The maximum photomodulation depth at quarter-wave optical bias point is better than 8%, and the contrast ratio is better than 80% at zero-wave optical bias point. The estimated radiation field focused at the sensor is about 1.8 kV/cm with a static voltage of 900 V across a 3.4 mm GaAs photoconducting emitter. The focus spot of the THz beam is about 1 mm. In a typical measurement, the signal-to-noise ratio can be better than 100,000. In order to use a lock-in amplifier which has 16 bit dynamic range, very low optical probe power is employed to avoid an overload problem in the lock-in. As one measurement, approximately 1–50 μW probe power was used. FIG. 12 is a plot of the signal versus peak power of the pump beam. The saturation starts at 1 MW/cm², which is due to the carrier screening effect.

Figure 13:
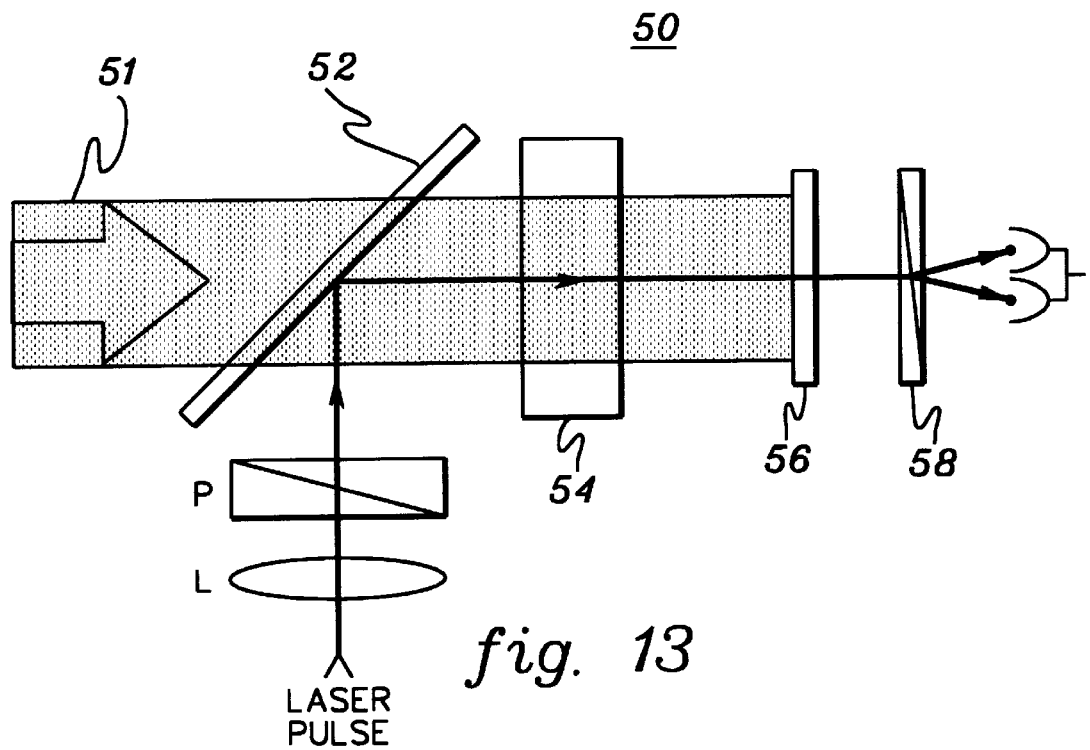
FIG. 13 depicts another embodiment of an electro-optic sampling apparatus in accordance with the present invention, wherein the optical probe pulse is again co-linear with the free space radiation as the radiation passes through the electro-optic crystal.

FIG. 13 depicts another embodiment of a co-propagating electro-optic sampling apparatus, generally denoted 50, in accordance with the present invention. In this simplified sensor arrangement, the femtosecond optical source is assumed to comprise a Ti:sapphire laser pumped by an Argon ion laser. The terahertz field might be generated from an unbiased GaAs wafer (not shown) with optical incidence at the Brewster angle. A one inch pellicle beam splitter 52, which is transparent to the terahertz pulse 51 propagating from left to right, directs the synchronized optical probe beam 53 co-linear along the terahertz pulse. A lens (L) (f=1 m) is placed in the probe beam path, but no lens is used for the pump or terahertz pulse. The diameter of the unfocused terahertz pulse and the pre-focused optical probe beam on the electro-optic crystal 54 are about 10 mm and 0.2 mm, respectively. The probe beam spot (0.2 mm) is comparable to the terahertz wavelength, i.e., the wavelength of 1 THz is about 0.3 mm in air.

A quarter-wave plate (λ/4) 56 is used to provide an optical bias to the probe beam which allows the system to be operated linearly. A Wollaston polarizer (WP) 58 is used to convert the induced phase retardation of the probe beam into intensity modulation on two mutually orthogonal linearly polarized beams. Two photodiodes (e.g., Model No. S5533, marketed by Hamamatsu Corp. of Bridgewater, N.J.) connected in an unbiased mode (e.g., similar to a Hamamatsu Corp. custom balanced photodiode type S1446) are used to detect optical intensity modulation. The dark current of the detectors is less than 0.1 pA under the unbiased condition.

Several materials have been tested as sensor crystals, including ZnTe, CdTe, ZnSe, GaAs, CdZnTe, LiTaO₃, LiNbO₃, BGO, BTO, GaP, BaTaO₃ and organic DAST crystals. Birefringent crystals (LiTaO₃, LiNbO₃ and DAST) have large polarization fluctuation due to the different temperature dependencies of the two refractive indices. This polarization fluctuation translates into intensity noise after the Wollaston polarizer. Test results have shown the ZnTe crystal to have best sensitivity, bandwidth and stability characteristics for the present invention.

Figure 14:
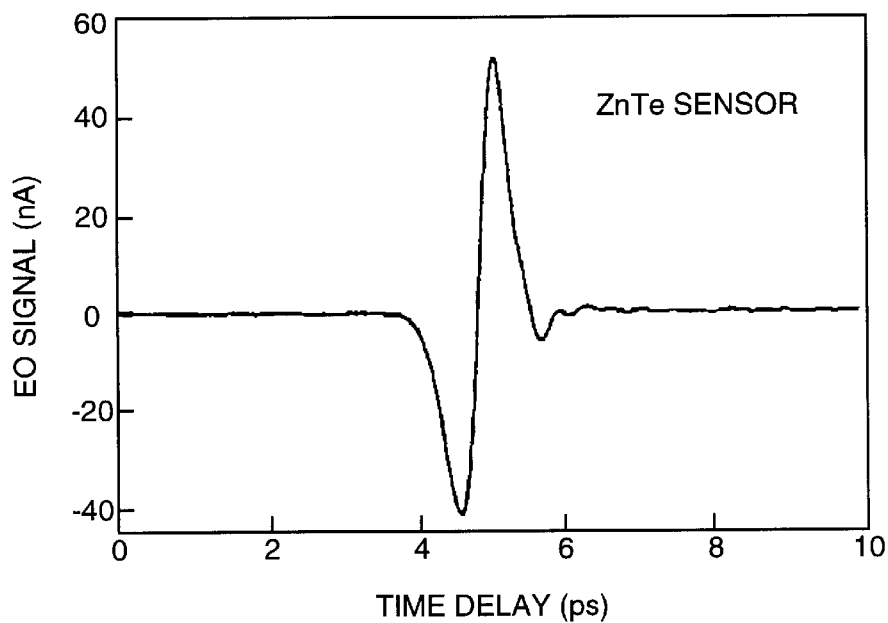
FIG. 14 is a graph of a typical radiation waveform measured using a 1.5 mm thick $\leq 110 \geq$ oriented zinc telluride (ZnTe) crystal in accordance with the present invention.

FIG. 14 depicts a typical radiation waveform measured by a 1.5 mm thick ≦110≧ oriented ZnTe crystal. The average optical excitation power incident on the GaAs emitter was 535 mW with an optical probe power of 2 mW. With the use of a lock-in amplifier (e.g., type SRS 850) with a time-constant of 0.3 s, the waveform has a signal-to-noise ratio (SNR) ≧3000. If the photodetector connects directly to an oscilloscope without the use of a lock-in amplifier and averaging, a real-time measurement at 40 waveforms per second with an SNR ≧ 50 and a 10 ps temporal window (time delay) displayed on the digital oscilloscope can be achieved.

The use of an electro-optic sensor for terahertz field measurements requires much less optical probe power than a photoconductive antenna based system such as described in the existing literature. This is because PIN (p-type semiconductor on intrinsic semiconductor on n-type semiconductor) photodiodes can be used in free-space electro-optic sampling. In general, the light sensitivity of a photodiode is much higher than conventional ultrafast photoconductive antennas. Limited carrier mobility, coupling efficiency, and the thin optical absorbing layer together operate to limit the responsivity of the ultrafast photoconductive antenna.

Again, the simplicity of the detection geometry, capability of optical parallel processing, and excellent signal-to-noise ratio make the present invention attractive for real-time, two-dimensional coherent far-infrared imaging applications. For example, a system can be constructed to convert a spatial and temporal electric-field distribution (far-infrared image) into an optical image by using an electro-optic crystal plate and a photodiode array, or a CCD camera.

Figure 15:
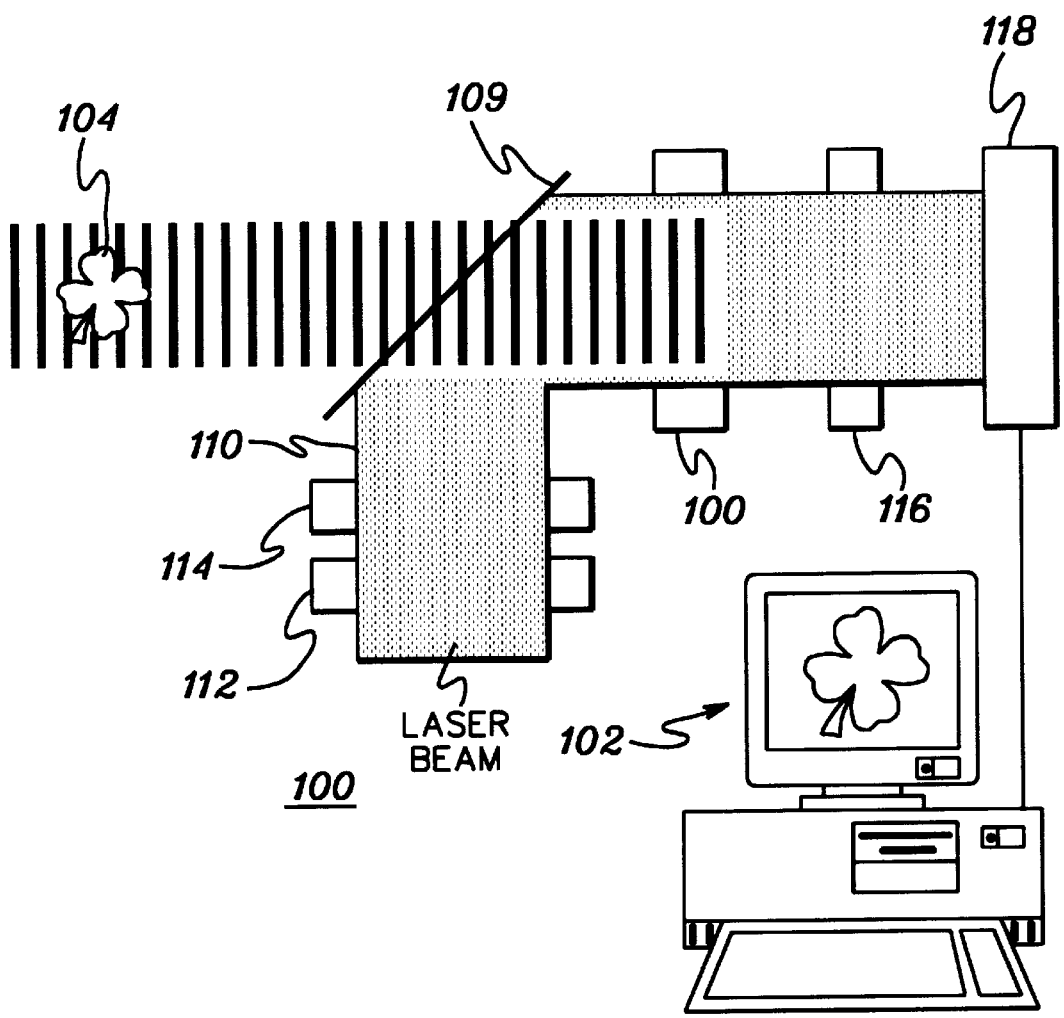
FIG. 15 is a depiction of one embodiment of a two-dimensional far-infrared imaging application in accordance with the present invention.

One embodiment of such a system, generally denoted 100, is depicted in FIG. 15. This system displays on a computer monitor 102 the two-dimensional field distribution transmitted through a sample object 104, which might comprise a leaf. The frequency range of the signal transmitted through the sample object can be from gigahertz to terahertz. After passing through the sample object, the electric field beam is incident on a relatively large electro-optic crystal 106, thereby changing the crystal's index of refraction as described above. One appropriate crystal 106 would be a ≦110≧ ZnTe crystal.

Optical beam 110 comprises a processed laser beam which is passed through a polarizer 112 and a compensator 114 for processing as described above in connection with FIGS. 1 & 4. The optical probe beam is reflected 109 to be co-linear with the electric field distribution as the distribution passes through the large electro-optic crystal 106. Again, by establishing co-linearity, a longer radiated field-optical beam interaction length is attained such that the geometry is capable of use for imaging an object, e.g., human tissue.

Note that the general concept of detection using a counter-propagating geometry is widely used in time-resolved far-infrared spectroscopy. However, since the terahertz beam and optical beam are incident from opposite directions, if an array of optical beams is used instead of a single beam, as in the case of an imaging application, then the configuration is not practical. Again, to overcome this limitation, described herein is an imaging application wherein the optical probe and the terahertz beam propagate co-linearly through the electro-optic crystal. The optical probe beam probes the electric field's spatial and temporal distribution in the crystal. An average probe power of 100 mW provides an image of 256×256 pixels at 50 pA signal current per pixel (assuming 1.5 µW/pixel at 42 µA/W slope and a 80% light fill factor) with a SNR ≧200. After passing through a polarizer 116, which checks the polarization rotation of the optical probe beam, the signals are collected in parallel by a CCD camera 118 and fed digitally to computer 102 for signal processing, i.e., data analysis (e.g., data averaging), frequency analysis, color coding and display of information. If the spatial resolution is limited by the terahertz wavelength (300 micrometers), this image has a size of 7.6×7.6 cm. A three inch GaAs wafer may be suitable as an electro-optic sensor if the transmitted electro-magnetic radiation (THz pulse) is loosely focused on the wafer. Two-dimensional or spatial imaging is possible because the sensor crystal is relatively large and because there is an array of detectors simultaneously receiving many single pixel waveforms.

Figure 16:
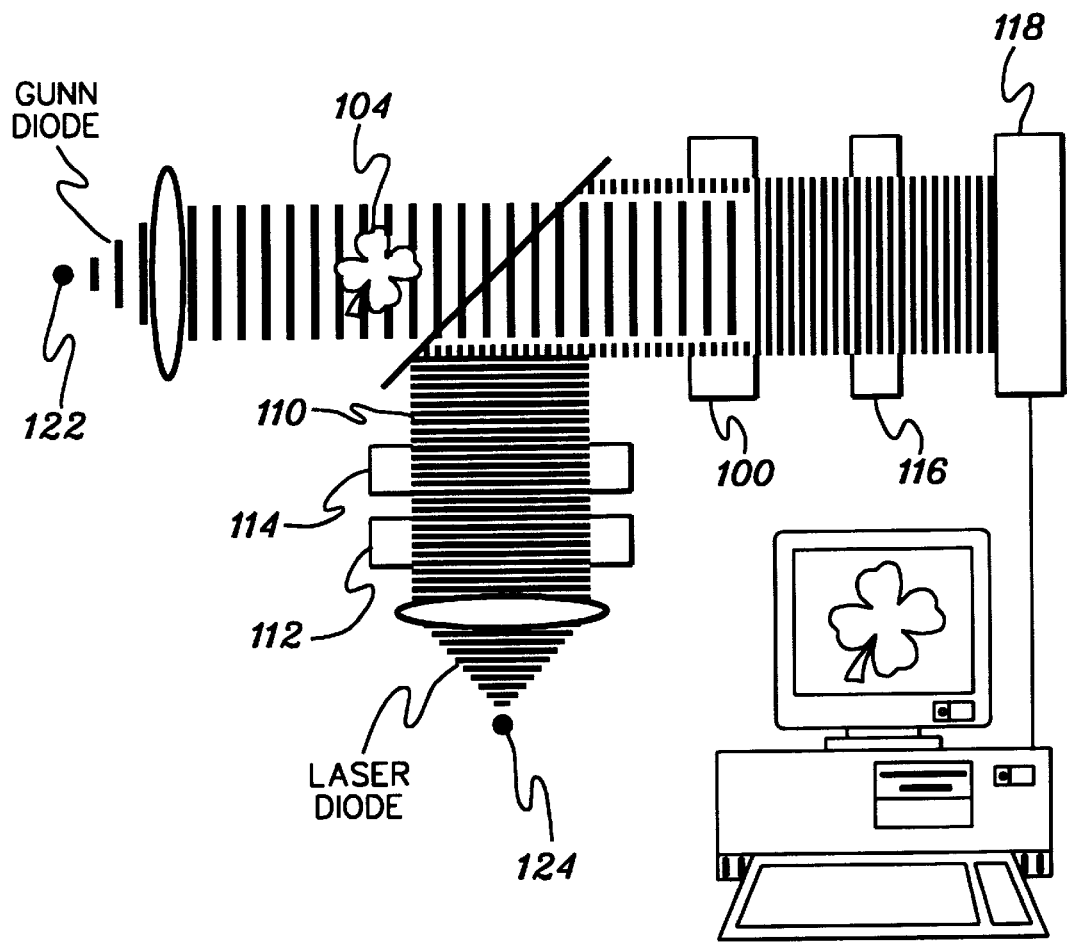
FIG. 16 depicts an alternate embodiment of a two-dimensional far-infrared imaging application in accordance with the present invention.

FIG. 16 is analogous to the imaging system of FIG. 15 except continuous electromagnetic waves are provided by a gunn diode 122, and a laser diode 124 provides the optical probe beam. In this configuration, the gunn oscillator is tuned at a specific frequency which is sensitive to the sample under test. Radiation passing through the sample is incident on the electro-optic sensor 100 within which the optical probe beam, again disposed co-linear with the radiation passing through the electro-optical crystal, measures the field strength in the sensor. The optical probe beam carrying the radiation field strength information from the sensor is detected by a CCD or diode array 118.

Figure 17:
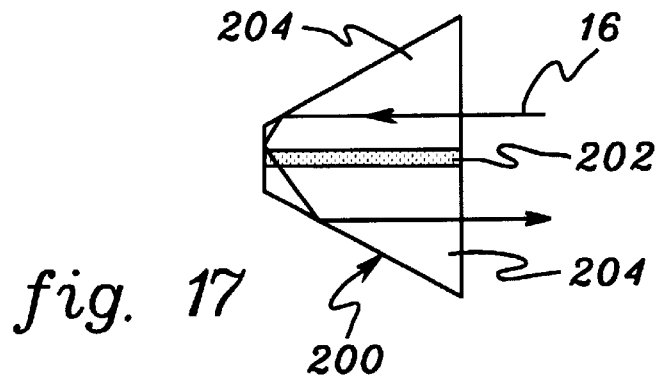
FIG. 17 depicts an alternate embodiment of an electro-optic crystal for use in an electro-optic sampling apparatus such as depicted in FIG. 1.
Figure 18:
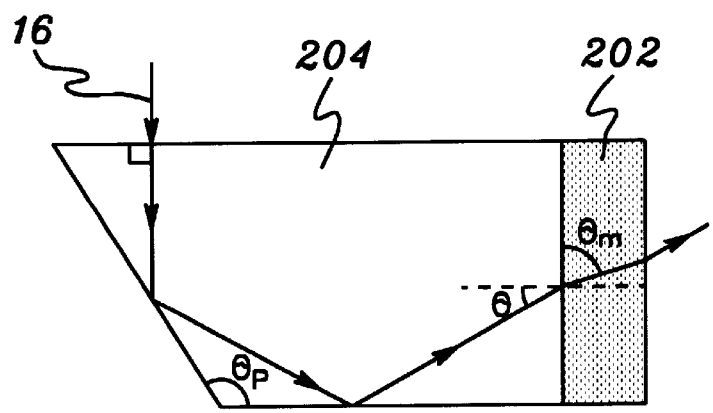
FIG. 18 is an enlarged perspective view of the optical beam reflecting within the fused silica and $LiTaO_3$ of FIG. 17.
Figure 19:
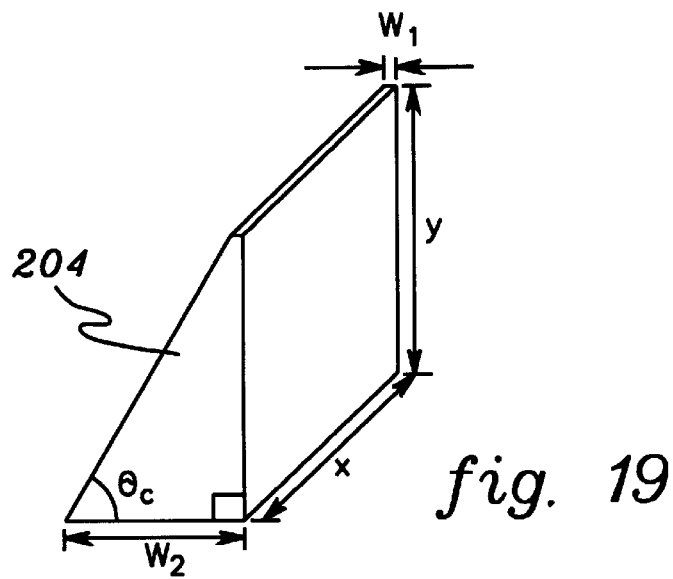
FIG. 19 is an enlarged view of one embodiment of a fused silica prism such as used in the electro-optic crystal of FIG. 17.

As noted briefly above, an alternate crystal geometry is depicted in FIG. 17 for use in a sensing apparatus such as FIG. 1 wherein the optical probe signal is incident on the electro-optic crystal in a direction counter to the direction of the electromagnetic field passing through the crystal. This crystal, generally denoted 200, comprises a thin lithium tantalate plate 202 sandwiched between two fused silica prisms 204. FIG. 18 comprises a partially enlarged view of the optical probe signal 16 passing through crystal 200, while FIG. 19 depicts in enlarged view one embodiment of the silica prism 204 employed in the electro-optic crystal assembly 200. As one specific embodiment, the thin lithium tantalate plate 202 might be 100 microns thick, while dimensions for prism portion 204 could comprise: x=2 mm, y=3 mm, W$_1$=0.1 mm and W$_2$=~1.17 mm. In order to achieve a velocity matching, the optical probe beam and the terahertz beam should intersect at an angle of 70.8°. For lithium tantalate, n(800 nm)=2.16, ∈=43, velocity matching between terahertz wave and an optical wave requires that the angle between them be:

$$\theta_m = \cos^{-1}\left(\frac{n}{\sqrt{\epsilon}}\right) = \cos^{-1}\left(\frac{2.16}{\sqrt{43}}\right) = 70.8° \quad (1)$$

The incident angle that the fused silica and lithium tantalate interface is:

$$\theta = \sin^{-1}\left(\frac{n}{n_f}\sin 19.2\right) = \sin^{-1}\left(\frac{2.16}{1.45}\sin 19.2\right) = 29.3° \quad (2)$$

While angle $\theta_p$ of the fused silica prism is determined by:

$$\theta_p + \theta = \pi - \theta_p + \frac{\pi}{2} \Longrightarrow \theta_p = \frac{270 - \theta}{2} = 120.4° \quad (3)$$

The critical angle of fused silica is 43.6°, and therefore the optical probe beam is guided in total internal reflection mode within the prism assembly 200. Reflection in the interface between fused silica and lithium tantalate is approximately six percent.

Due to the waveguide effect and the dispersion of lithium tantalate in the terahertz regime, distortion-free detection is possible up to 3 THz. The advantages are that: lithium tantalate has an electro-optic coefficient 10× higher than that of GaAs; after interacting with the optical beam, the terahertz beam propagating inside the crystal no longer contributes to the electro-optic signal since terahertz dispersion is limited to a traveling distance three times shorter than that of the optical beam; the short effect of travel distance of the terahertz beam is advantageous in connection with the tight focusing of the silicon lens; depending on the dimension of the crystal, the reflection-free time window can be longer than 800 ps, which is unmatched using other sampling geometries; and since the optical beam scans across the terahertz beam, frequency-dependent terahertz spot size caused by the focusing of the silicon lens is averaged out, giving a better frequency response.

Figure 20:
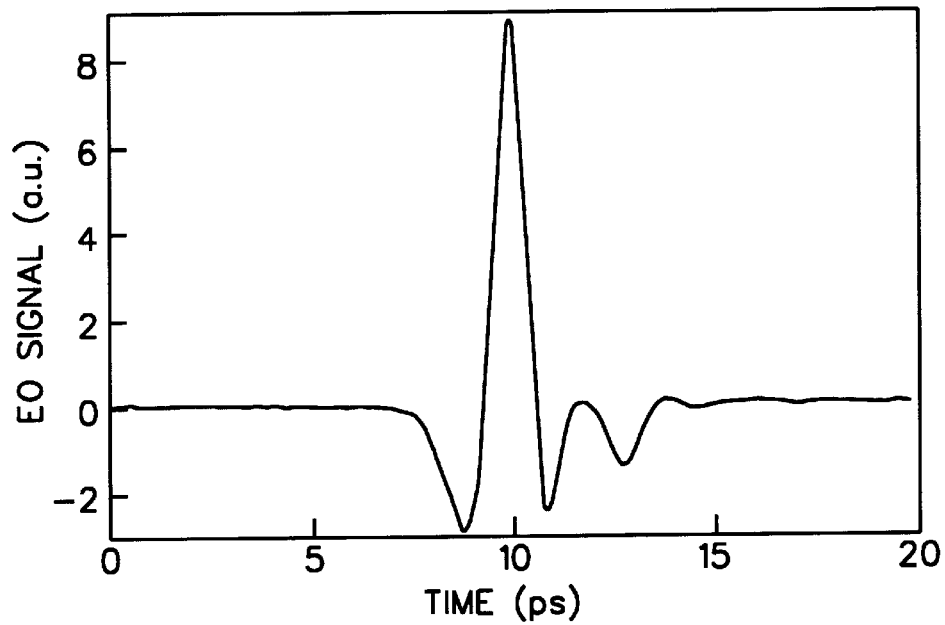
FIG. 20 depicts a transient waveform comprising a plot of electro-optic signal strength versus time delay employing the crystal of FIG. 17.
Figure 21:
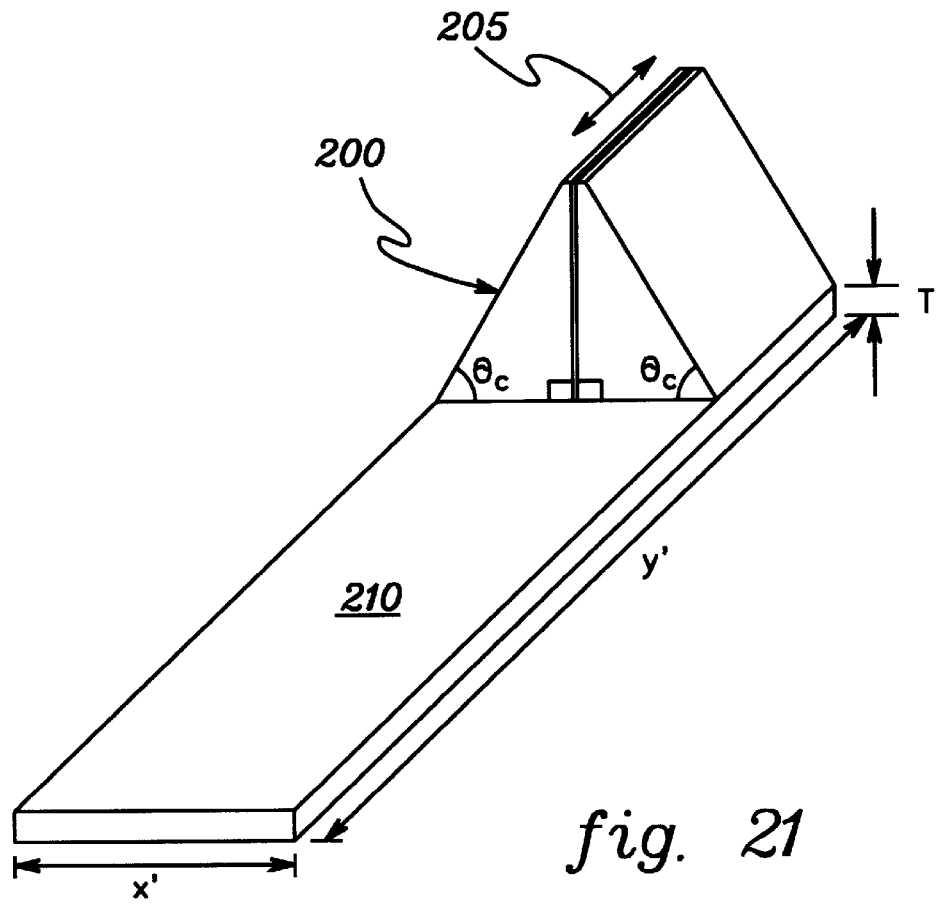
FIG. 21 depicts the electro-optic crystal of FIG. 17 disposed on a fused silica handle and showing the orientation of the optical axis of the crystal.

FIG. 20 is a graph of a transient waveform comprising a plot of electro-optic signal strength versus time delay employing a crystal assembly such as depicted in FIG. 17. Finally, an enhanced embodiment of crystal assembly 200 is depicted in FIG. 21 wherein a fused silica handle 210 attached to the base of the crystal is provided to facilitate handling thereof. The orientation of the c-axis of the crystal is designated by arrows 205. As a specific example, dimensions for handle 210 might comprise x'~3.4 mm, y'=10 mm and T=0.5 mm.

One of the major advantages of free-space electro-optic (EO) sensors for the characterization of terahertz beams is the ultrabroad frequency bandwidth employable. In one embodiment, applicants have produced coherent detection of mid-infrared terahertz beams up to 37 terahertz. This represents a significant improvement.

For most EO sensors, phonon absorption imposes an upper limit of less than 10 terahertz. Beyond the Reststrahlen band, however, most semiconductor EO materials are transparent all the way to near-IR. This promotes the possibility of free-space EO sampling in the mid-IR region. Bonvalet et al. have demonstrated the generation of a mid-infrared terahertz beam via optical rectification using a 15 fs laser, see "Applied Physics Letter," volume 67, pp 2907 (1995), which is hereby incorporated herein by reference in its entirety. Combined with this terahertz source, the EO sensors could be used in various coherent spectroscopies.

Frequency response of EO sensors is mainly determined by the mismatching of optical group velocity and the frequency-dependent terahertz phase velocity. The optimum thickness of a ZnTe sensor is about 20 micrometers for mid-IR detection.

The experimental setup included a mode locked Ti:sapphire laser to generate 12 fs laser pulses with average power of about 500 mW. 350 mW of the laser power was focused on the <110> oriented GaAs emitter by an off-axis parabolic mirror with a 5 cm effective focal length. The broadband terahertz radiation was collimated and then focused by a pair of f/0.6 parabolic mirrors on the EO sensor. The laser probe beam was combined to colinerally travel with the terahertz beam through a 2 micrometer thick pellicle, which has a negligible effect on laser pulse width and terahertz beam. The EO modulation induced by the ultrafast Pockels effect was detected by using a pair of balanced photodiodes. Detection sensitivity of photo-modulation ($\Delta I/I$) as small as $2\times 10^{-8}$ $Hz^{-1/2}$ was routinely achieved. By varying the delay between the pump and probe pulses, the time domain waveform of the mid-IR transient can be mapped out.

Figure 22:
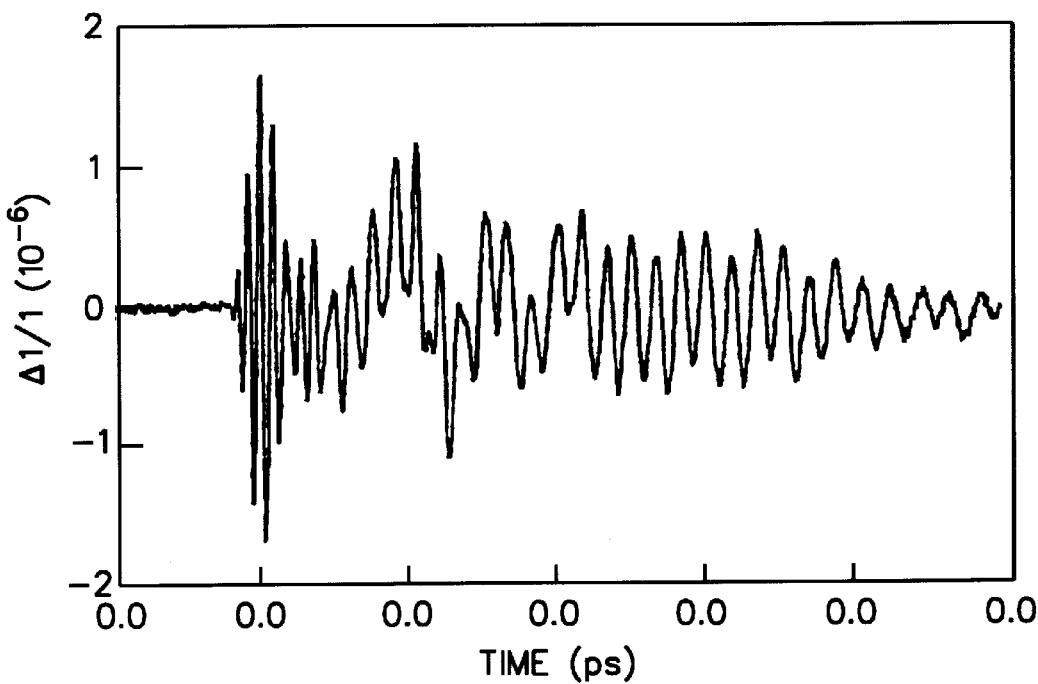
FIG. 22 depicts a temporal waveform of terahertz radiation measured by a 20 μm ZnTe sensor, the shortest oscillation period being 31 fs.
Figure 23:
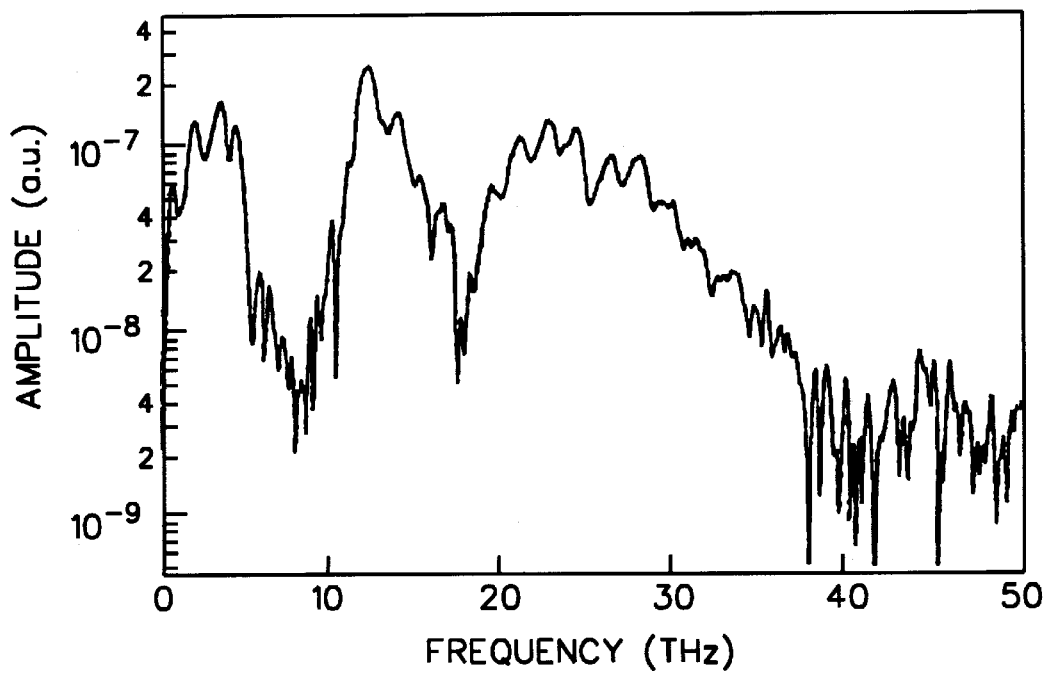
FIG. 23 depicts the frequency spectrum of the waveform of FIG. 22, the absorption from 5 THz to 10 THz is due to the emitter (GaAs) and the sensor (ZnTe)

FIG. 22 shows a typical waveform obtained in a single scan with a 300 ms lock-in time constant. A 0.45 mm thick <111> GaAs was used as an emitter and a 20 micrometer thick <110> ZnTe crystal as an EO sensor. The terahertz pulse is clearly chirped, with high frequency components traveling faster than the low ones. The chirping occurs when the terahertz pulses generated on the front surface of GaAs propagate through the rest of the material. The shortest period of the oscillation is 31 fs. Fourier transform of the waveform is shown in FIG. 23, where the highest frequency response reaches 37.3 terahertz. The gap between 5 terahertz to 10 terahertz is due to the Reststrahlen ends of ZnTe and GaAs, while the frequency dip around 17 terahertz is under analysis. The preliminary result demonstrates the advantages of using the linear electro-optic effect (Pockels effect) for the measurement of ultrafast far-infrared to mid-infrared pulsed electro-magnetic radiation.

The use of a high-repetition-rate (250 kHz) regenerative amplified laser with $\mu J$ pulse energy in a free-space terahertz (THz) beam electro-optic sampling system has produced a significant improvement in both the signal-to-noise ratio ($>10^5$) and absolute probe beam photomodulation depth ($>8\%$). Focal plane images of the electric field distribution (strength and polarity) in dipole and quadrupole planar photoconductive emitters are next presented. Preliminary results of real-time 2-D THz images of moving objects have been obtained.

The use of a chirped pulse regenerative amplifier (Clark MXR) at 1 kHz repetition rate for the detection of high power THz pulses by phase retardation in a $LiTaO_3$ crystal has been demonstrated. The signal-to-noise ratio (SNR), however, has been limited by the low repetition rate, the sensor crystal, and the geometry of the polarizer arrangement. We now report the use of a high-repetition rate regenerative amplified laser for the generation and detection of free-space THz radiation in a free-space electro-optic sampling (FS-EOS) system using ZnTe sensor crystals. The use of a high pulse-repetition-rate, $\mu J$ pulse energy laser to replace the usual low peak power laser oscillator or low repetition rate regenerative amplifier, marks a significant improvement over previous FS-EOS systems, especially in the application of real-time THz imaging of moving objects. Far-field radiation images of dipole and a quadrupole THz photoconductive emitters are presented as a demonstration of this potential.

Figure 24:
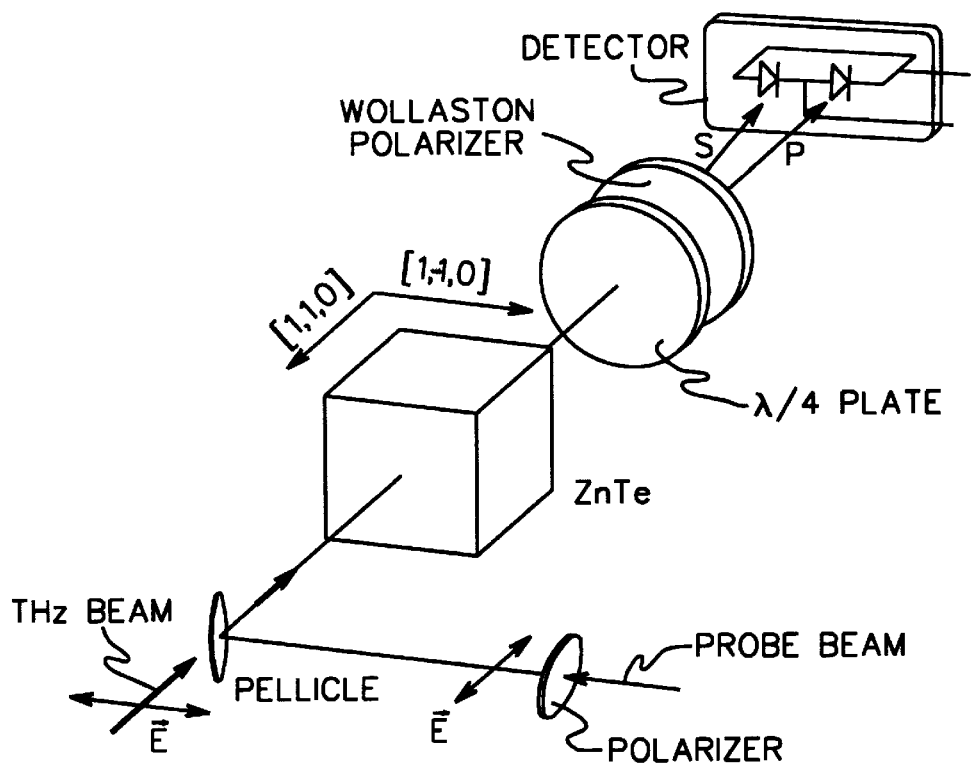
FIG. 24 is a diagram of one embodiment of free-space electro-optic sampling in accordance with the present invention employing a high-repetition-rate regenerative amplified laser.

The core of the improved time-resolved THz imaging system consists of an amplified optical source and a FS-EOS unit. The former is a Ti:sapphire regenerative amplifier system (Coherent RegA 9000) with a 250 kHz repetition rate, 3 $\mu J$ pulse energy, and 200 fs pulse duration at 800 nm. FIG. 24 shows the sampling unit using a balanced photodetector. This system is similar to previously reported systems which were based on unamplified sources; i.e.: Coherent MIRA 900; and Spectra-Physics Tsunami. A 2 $\mu m$ thick pellicle beamsplitter, which is transparent to the terahertz beam, is used to reflect 50% of the synchronized optical probe beam colinearly along the THz beam. The polarization of both the THz and optical probe beams are aligned parallel to the [1,−1,0] direction of a 1.4 mm thick <110> oriented ZnTe sensor crystal. Following the sensor, a quarter-wave plate is used to impart a $\pi/4$ optical bias to the probe beam, which allows the system to be operated in the linear range. A Wollaston polarizer is used to convert the THz field induced phase retardation of the probe beam into an intensity modulation between the two mutually orthogonal linearly polarized beams. A pair of silicon PIN photodiodes (EG&G C30808E) connected in a balanced mode is used to detect the optical intensity modulation. The typical noise current from the balanced photodiodes, as measured by a digital lock-in amplifier (SRS 850) is a several pA (300 ms time constant), while the signal current from a focused THz beam can exceed several $\mu A$. Since the dynamic range of the digital lock-in amplifier is only 16 bit, with a full-scale read-out current of 2 $\mu A$, in order to measure dynamics close to 10,000,000 (~23 bit) corresponding to a maximum signal current greater than 30 $\mu A$, a 100 k$\Omega$ resistor, connected in parallel to the lock-in amplifier, is used to reduce input impedance.

Figure 25:
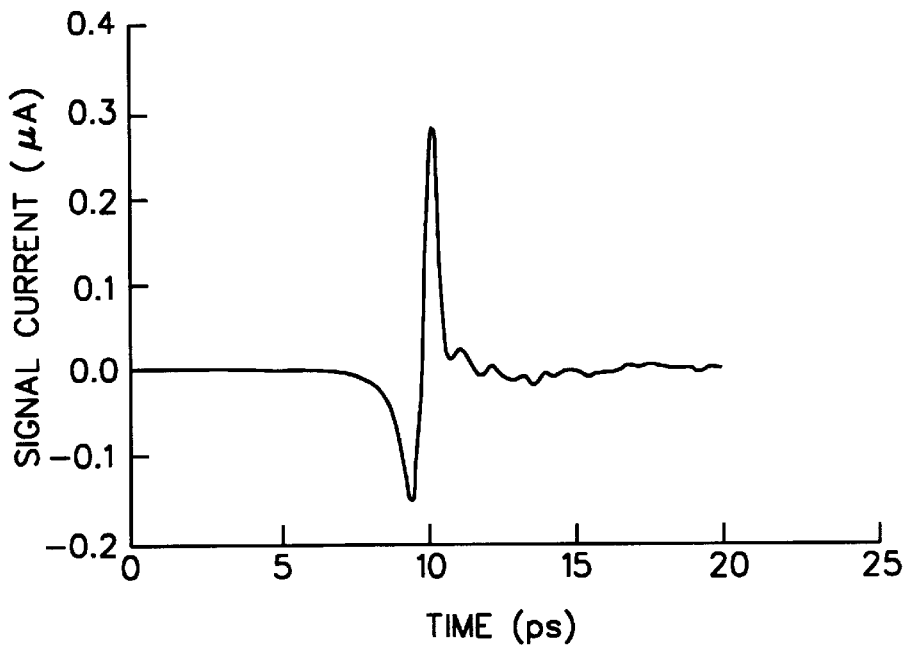
FIG. 25 comprises a temporal waveform of terahertz radiation measured by the balanced detector at quarter-wave optical bias of FIG. 24.
Figure 26:
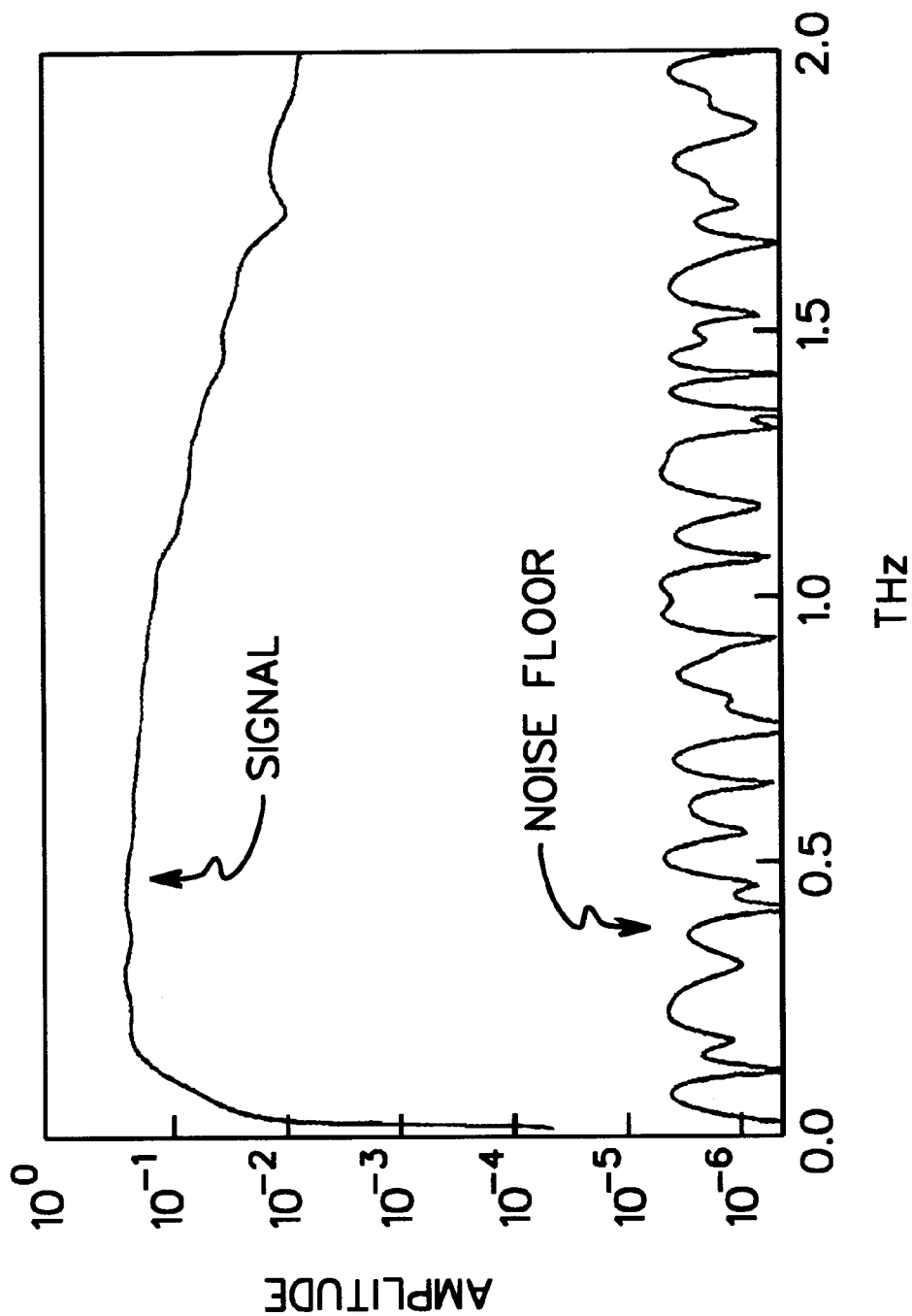
FIG. 26 is a plot of the corresponding frequency spectra (FFT) of the temporal waveform of FIG. 25, as well as noise.

Using a 2-mm GaAs photoconductive emitter with a bias field of 2.7 kV/cm and a 1.4 mm thick <110> ZnTe sensor, the maximum modulation depth of the probe beam after the analyzer, measured by the balanced photodiode is 7.7%. These values correspond to a peak THz field of 1.6 kV/cm in the ZnTe sensor. FIG. 25 plots a typical temporal signal of the THz radiation as measured by the balanced detector (photocurrent). The average pump power on the GaAs photoconductor is 240 mW at normal incidence and the average probe power (after the ZnTe crystal) is about 36 $\mu W$. The diameter of the focused THz beam and the optical probe beam on the ZnTe crystal is about 1.5 mm and 0.6 mm, respectively. The peak-to-peak signal current is 450 nA, and the peak-to-peak of the noise current is less than 4 pA, with its RMS noise of 1.6 pA. To better characterize the signal-to-noise ratio of the system, the frequency spectra of both signal and noise are plotted in FIG. 26. From 0.1 THz to 1.2 THz, the SNR (defined as the ratio of the THz field on/off photocurrent) is between 50,000 to 100,000. A thicker crystal, higher emitter bias field, and a tighter focus of the THz beam in the ZnTe sensor, results in a further increase in both the SNR and the absolute modulation depth.

Figure 27:
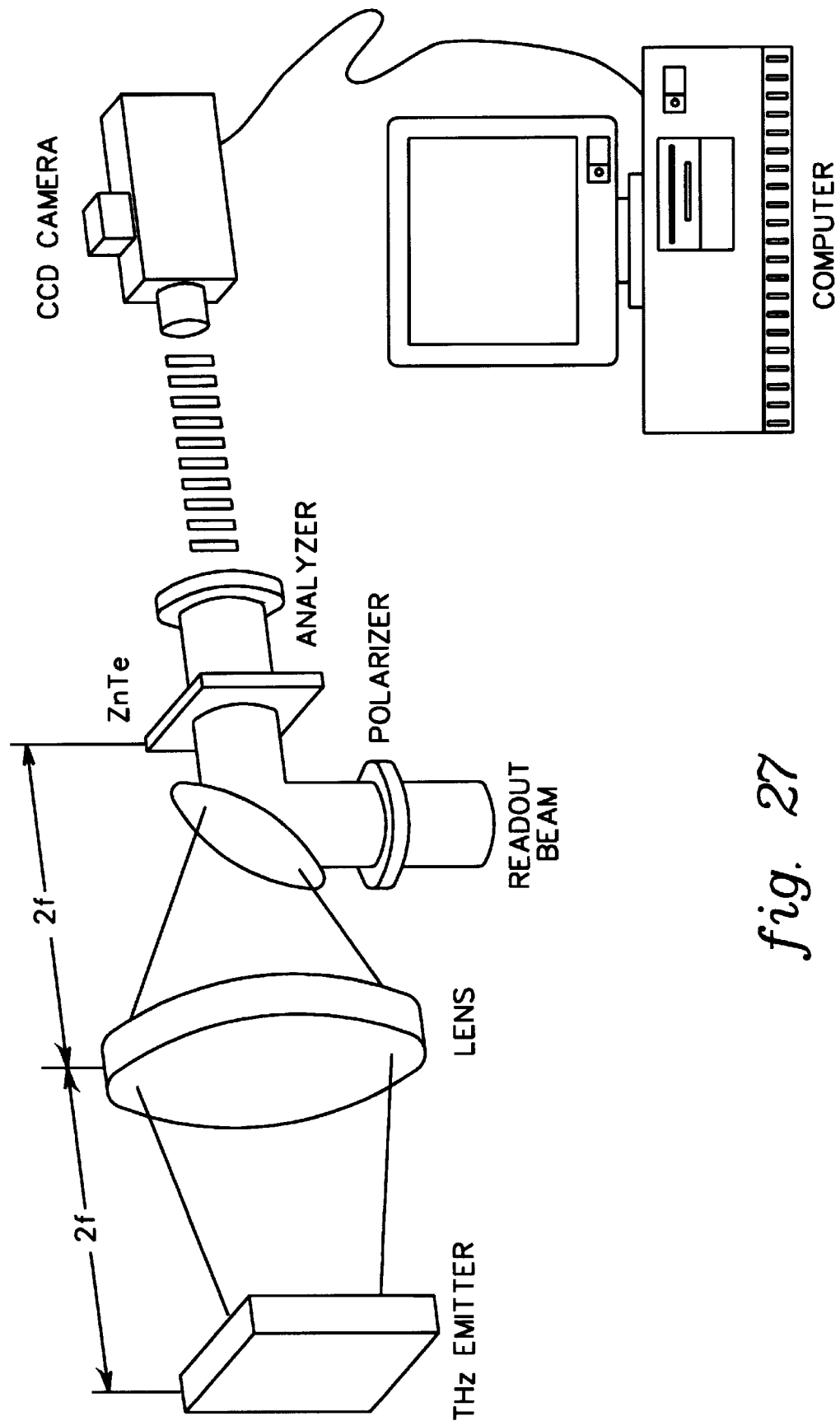
FIG. 27 is a diagram of one embodiment of terahertz imaging in accordance with the present invention wherein a 2-D distribution of far-infrared (THz) field is converted into an optical image as gated in the ZnTe crystal and measured by a CCD camera.

The excellent SNR and planar optical detection enable us to perform THz imaging. FIG. 27 shows the THz imaging setup. A 2-D distribution of the far-infrared THz field is converted into an optical image as sampled in the ZnTe crystal and measured by a CCD camera. Typically, the THz beam source is a large-aperture planar GaAs photoconductor, and a 2" silicon lens or pair of off-axis 2" parabolic mirrors are used to collimate and focus the THz radiation. For the imaging experiment, due to the small full-well capacity of the common CCD pixel, the CCD can be easily saturated by the background light. Therefore, the previously mentioned quarter-wave plate is removed to reduce the background light. The largest relative photomodulation depth with a focused THz beam from this arrangement (near zero optical bias) is better than 50%. However, with a large cross-section THz beam, the typical photomodulation depth is between 10% to 30% and scattered light from defects in the ZnTe crystal is sufficient to keep the electro-optic detection nearly linear.

FIG. 28 plots the frequency spectrum (FFT) from one of the pixels at a focused THz point, and FIG. 28a is the temporal THz signal recorded from a single CCD pixel where data was taken from 100 sequential frames with a temporal step of 66.6 fs. Time-resolved images (288×384 pixels) are obtained by recording their consecutive frames. Unlike balanced detection, the lock-in amplifier cannot be used with the CCD arrays.

Figure 29A:
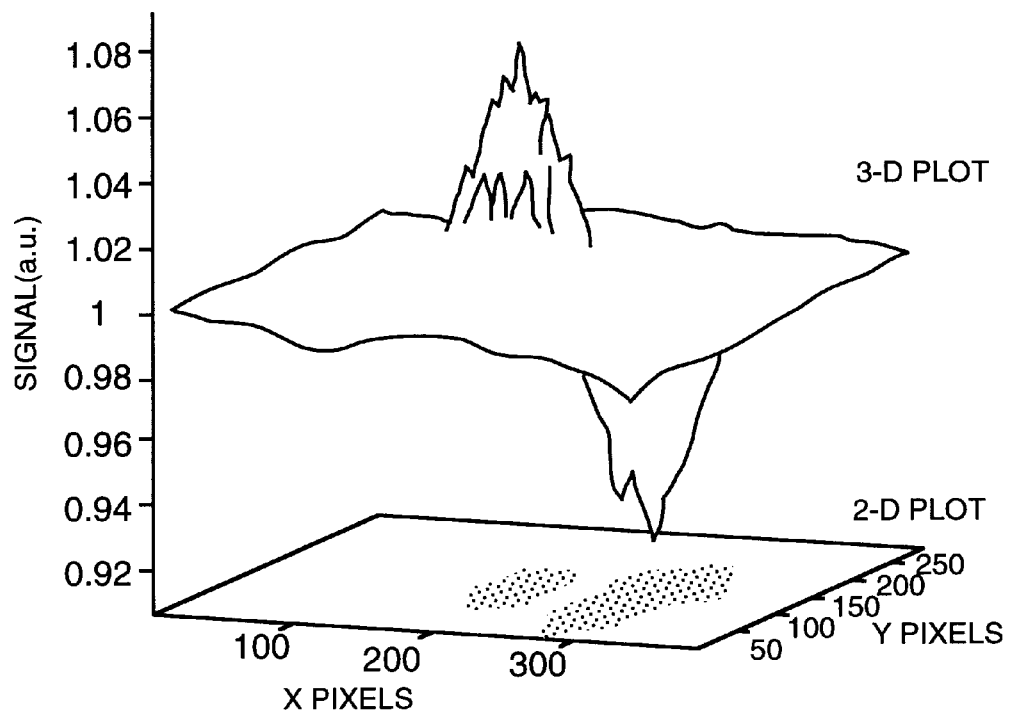
FIG. 29a comprises a 2-D plot and a 3-D plot of the focal-plane image of the terahertz field from the quadrupole of FIG. 29.
Figure 29:
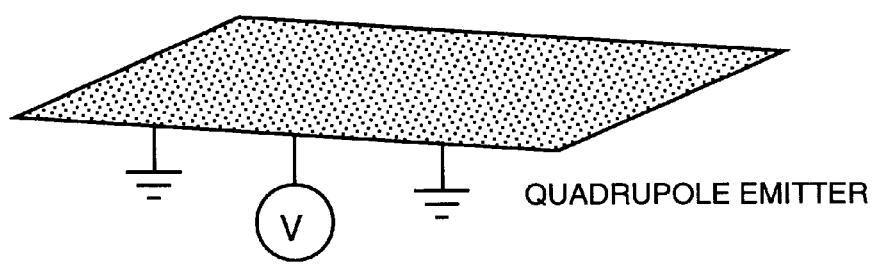
FIG. 29 depicts one embodiment of a quadrupole emitter having a center electrode biased and two side electrodes connected to ground.

We have imaged the field distribution from a planar quadrupole THz emitter. FIG. 29 shows the quadrupole emitter where the center electrode is biased and two side electrodes are connected to ground. The center electrode is 1 mm wide and has a length over 1 cm. The gaps between the side electrodes are 1.5 mm and 2 mm, respectively. This quadrupole geometry generates two unbalanced dipoles with opposite polarity. The peak field distributions are plotted in 2-D and 3-D in FIG. 29a. FIG. 29a clearly indicates the radiation pattern and the polarity of two opposite dipoles.

Figure 30A:
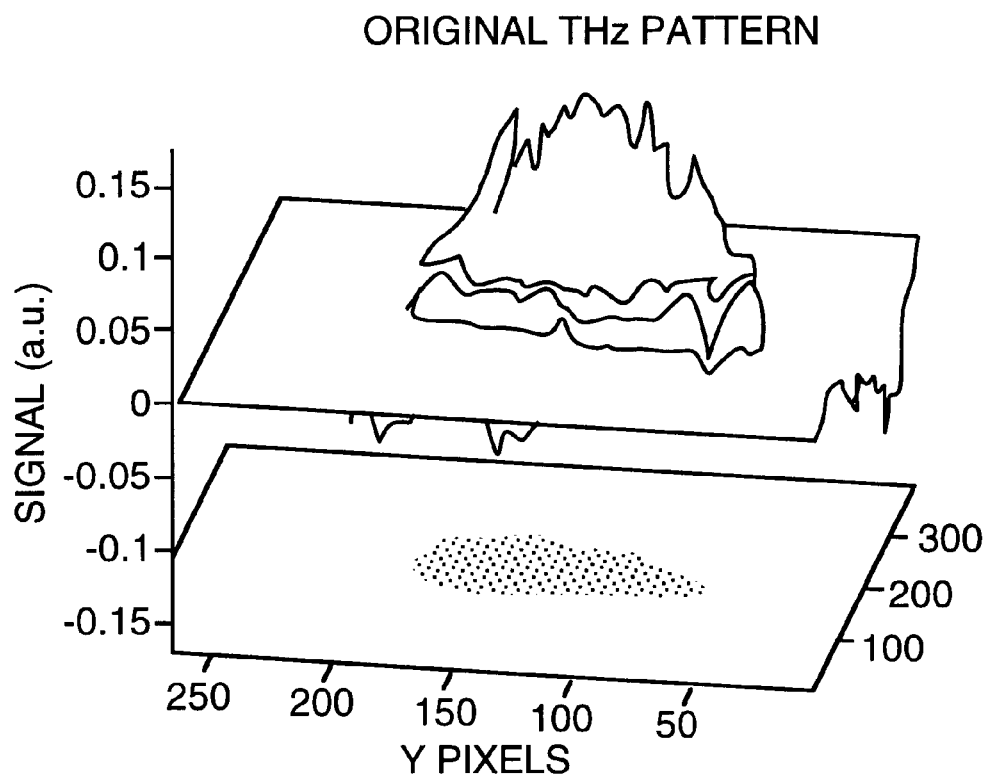
FIGS. 30 & 30a depict focal-plane images without a rod sweeping across the terahertz beam path in the focal plane.
Figure 30:
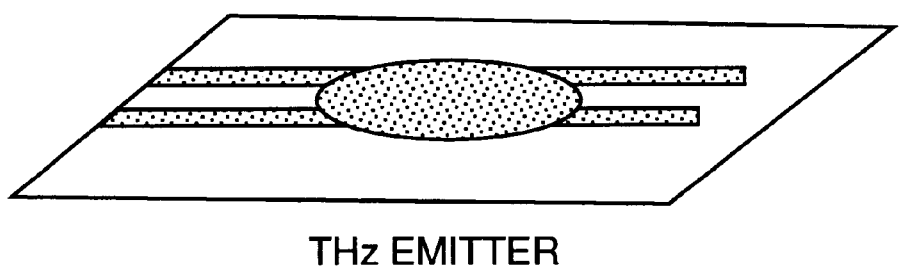
Figure 31A:
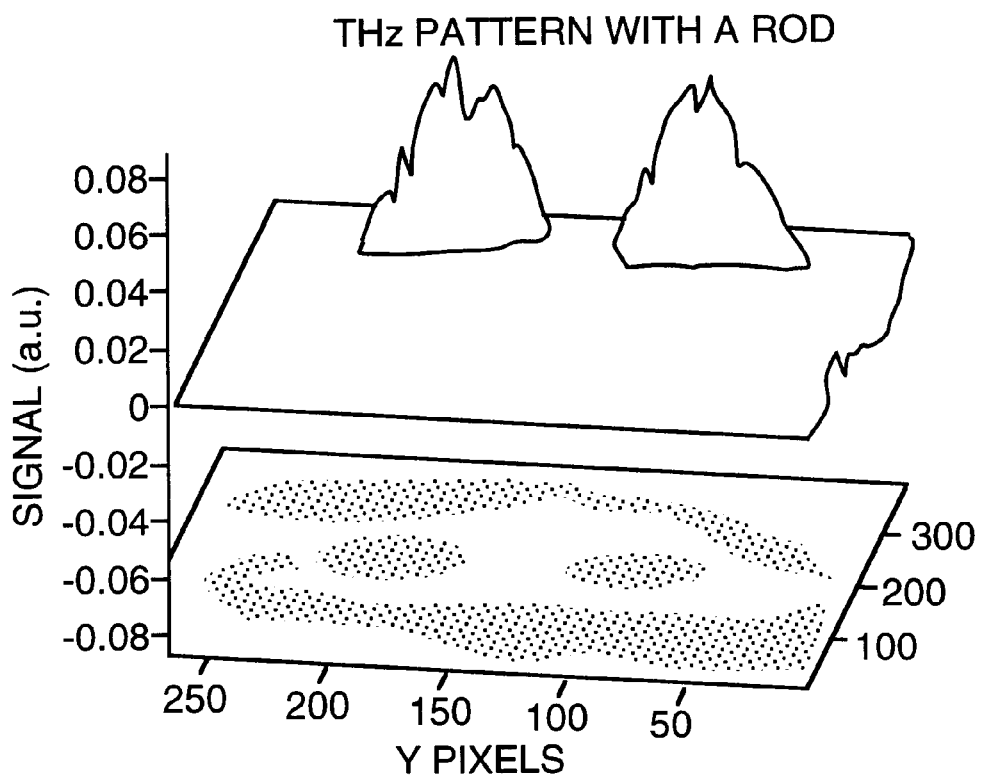
FIGS. 31 & 31a depict a 2-D and 3-D image of a rod swept through the terahertz beam path at the focal plane employing the imaging system of FIG. 27.
Figure 31:
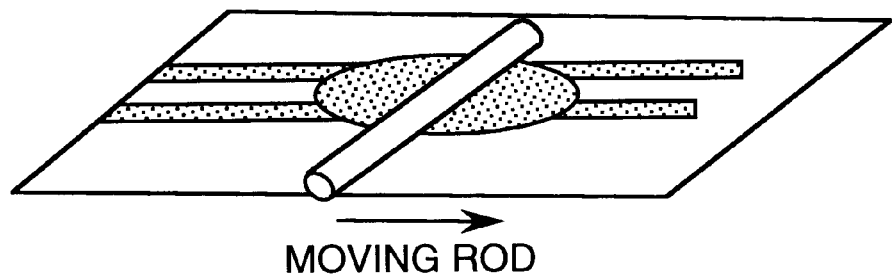

One of the most important applications of this free-space electro-optic THz imaging method is its ability to image moving or living objects. The images of a moving objective at focal-plane can be viewed at the video rate (38 frames/s). To demonstrate this ability, a dipole emitter (2×5 mm² photoconductor) was placed about 1 cm away from the focal-plane as the THz source, and an object was positioned in the focal-plane. FIGS. 30 & 30a show the original THz imaging pattern without an object in the imaging path, and FIGS. 31 & 31a capture an image when an object (a wooden rod with 2 mm diameter) was swept through the THz beam path at the focal-plane.

This system can also be used to record the dynamic radiating process resulting from varying the bias field until breakdown. The maximum frame transfer rate of our current CCD (Princeton Instrument, PentaMax) with a readout rate of 5 million pixels per second is 38 frames/second and can sustain up to 152 frames/second with 4×4 binning. The fastest frame transfer rate from some CCDs can reach upwards of 2000 frames/second making it possible to image real-time 2-D transient processes, including the THz radiation pattern from an explosion.

In conclusion, we have demonstrated the free-space electro-optic imaging using a regenerative amplified laser which combines both high repetition rate and high pulse energy. In this way, significant improvements in the imaging system have been obtained. Results of 2-D THz images (1 cm²) at the focal-plane, including the real-time images of moving objects, have been achieved.

In an alternate aspect, the present invention further comprises a free-space ultrafast magneto-optic sampling technique. Specifically, presented below is an ultrafast magneto-optic sampling system to characterize freely-propagating transient magnetic pulses. Presented are the direct experimental measurements of a time-resolved magnetic field associated with a terahertz beam.

Figure 32:
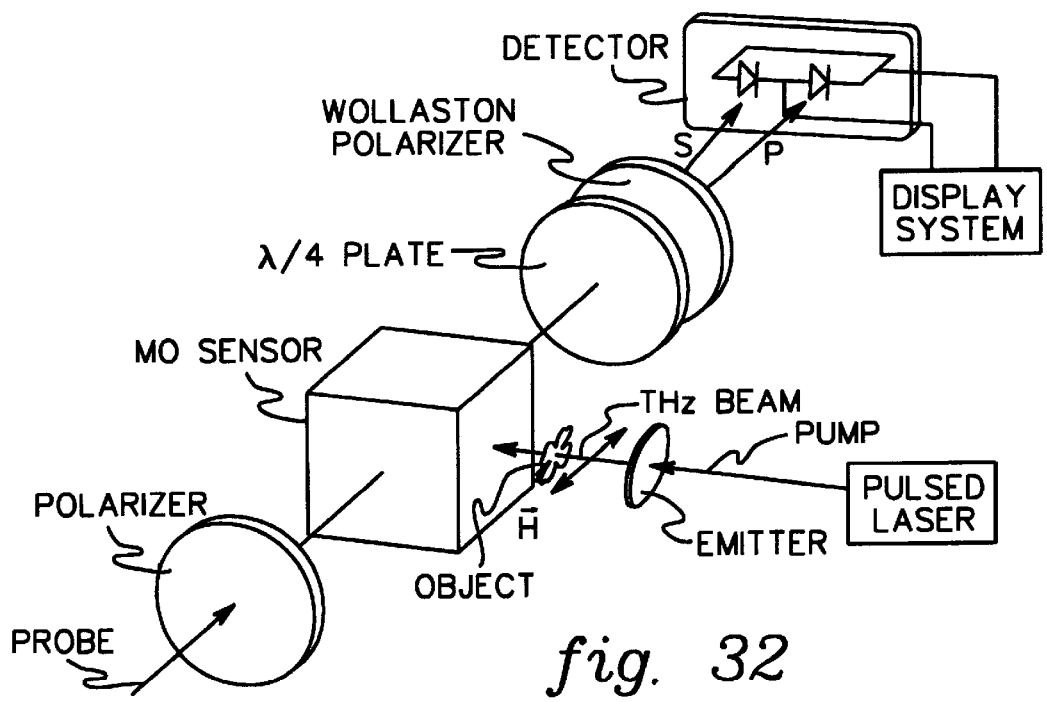
FIG. 32 is a diagram of one embodiment of an ultrafast free-space magneto-optic sampling apparatus in accordance with another aspect of the present invention.

FIG. 32 depicts an apparatus for ultrafast magneto-optic sampling in accordance with the present invention. The setup includes a Ti: sapphire laser regenerative amplifier (Coherent RegA) which provides pulses of 220 fs duration and 800 nm wavelength at a repetition rate of 250 kHz, providing 4 µJ/pulse. The peak power is 18 MW. The beam is split by a 95/5 beamsplitter into a time-delayed pump, which excites a biased GaAs emitter to produce terahertz radiation, and a weak probe beam, which measures Faraday rotation in the magneto-optic sensor crystal induced by the transient magnetic field. The configuration of the magneto-optic sampling geometry differs from the electro-optic sampling geometry. In this experiment, the terahertz emitter is placed several centimeters (1.5 cm to 5 cm) away from the sensor and in a perpendicular position relative to the propagation direction of the probe beam. Since this technique is governed by the Faraday effect, the magnetic component of the terahertz wave must prorogate colinearly with the probe wave to produce the index birefringence through, $$\theta \sim VBL \cos \gamma$$

With V being the Verdent constant, B is the magnitude of the magnetic field, L is the length of the crystal and $\gamma$ is the angle between the direction of the magnetic field and the direction of the probe beam (in this case, $\gamma=0$). The detection system of the probe beam, which is similar to the detection system for the electro-optic sampling signal, includes a pair of balanced detectors and a lock-in amplifier. The temporal waveform of the magnetic signal is recorded by scanning the time-delay of a computer-driven translation stage.

In free-space submillimeter-wave radiation, the pulse width of the magnetic component is as short as the electric component, and the amplitude ratio of the electric component to the magnetic component in a plane wave approximation is the speed of light in vacuum.

Figure 33:
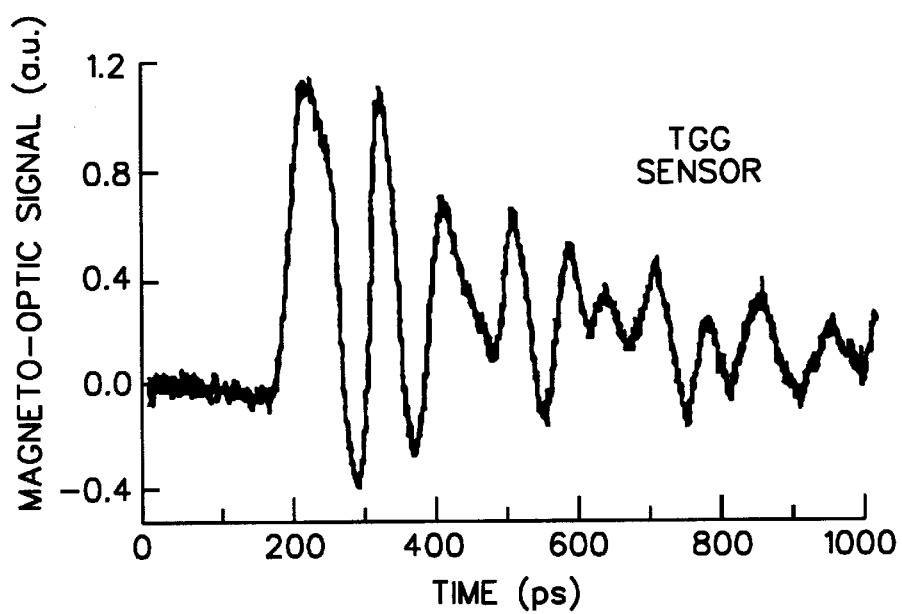
FIG. 33 is a plot of a temporal waveform of the magneto-optic signal (single scan) with terbium-gallium-garnet as the sensor.

Several magneto-optic sensors have been tested. One of the sensors selected is gerbium-gallium-garnet (TGG), which has a high Verdet constant (i.e., V=61 rad/T·m), a small optical absorption (~0.0015/cm), and a high thermal conductivity (K~7.4 W/K·m). A small optical absorption and a large thermal conductivity provide a homogeneous Faraday rotation in the crystal. FIG. 33 plots a temporal waveform of the magneto-optic signal (single scan) with TGG as the sensor. The current geometry does not satisfy the velocity-matched condition, with a measured risetime (10% to 90%) of 33 ps in FIG. 33. With a velocity-matched geometry the temporal resolution should be greatly improved.

Figure 34:
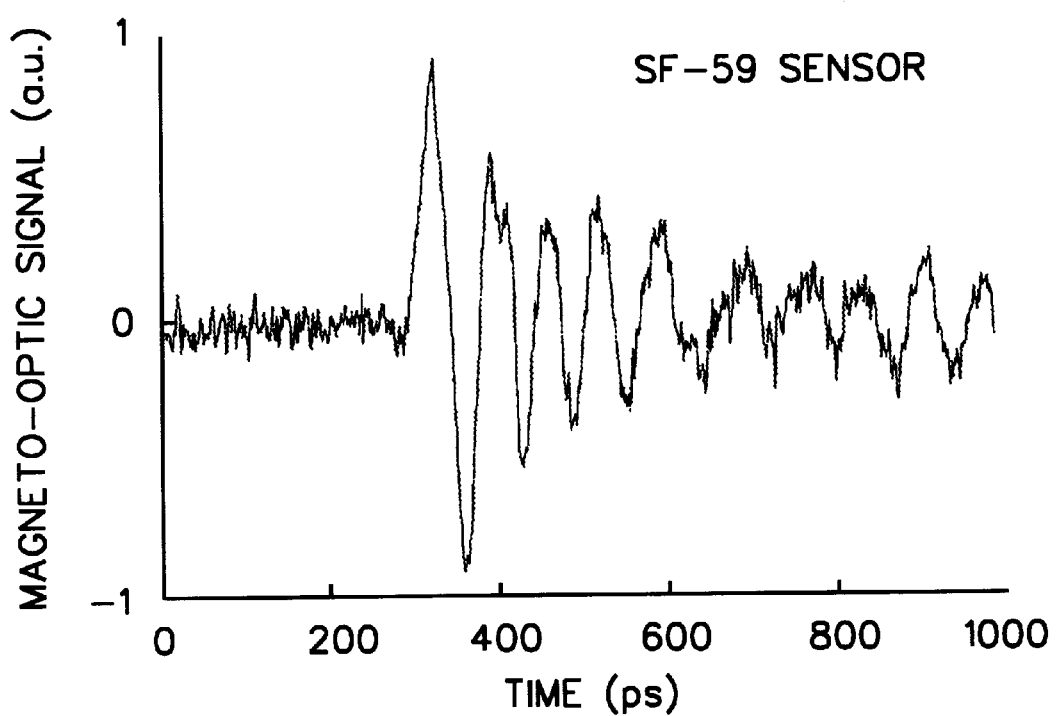
FIG. 34 is a plot of a temporal waveform of the magneto-optic signal with amorphous glass (SF-59) sensor.

Amorphous glass SF-59 behaves similar to that of TGG. FIG. 34 presents a 5-scan averaged response. The duration of the first peak (FWHM) is 21 ps, with a risetime (10% to 90%) of 22 ps. A smaller $\Delta I/I \sim 5 \cdot 8 \times 10^{-5}$ is due to the smaller Verdet constant of this material and a shorter interaction length of the material. The length of the SF-59 sensor is almost four times shorter than the TGG sensor. Rings in the waveform are mainly attributable to the same criteria discussed above. The overall response magnetic field sensitivity of TGG is about three times greater than SF-59.

Ultrafast magneto-optic sampling provides a novel technique to measure freely propagating magnetic transient signals. It is clear that free-space magneto-optic sampling will open a new field in the ultrafast sampling community. With the increase of sensitivity and bandwidth, free-space magneto-optic sampling comprises an ideal tool for the terahertz magnetic spectroscopy. This technique offers the coherent measurement of magnetic transient fields, which gives precise information of the phase and amplitude of the magnetic signal with enhanced temporal and spatial resolution. Also, the technique is believed useful for magnetic relaxation and resonance studies, time-resolved studies of magnetization transport and spin dynamics, investigations of the intrinsic dynamics of magnetic flux threading superconductors, as well as possible magnetic time-domain spectroscopy for investigations of the magnetic permeability and susceptibility of materials, and a novel magnetic imaging corresponding to the electro-optic imaging described above.

To summarize, a dynamic range of electro-optic field sensors is presented herein for the coherent detection of pulsed electromagnetic wave radiation. In contrast to pre-existing photoconductive antenna approaches, free-space electro-optic sampling in accordance with this invention separates the temporal detection from the amplitude detection by using the electro-optic crystal and the photodetector as described. This separation allows optimal performance of both the temporal resolution and the signal sensitivity to be achieved. Using a free-space electro-optic field sensor it is feasible to convert a far-infrared spatial and temporal image into an optical spacial and temporal image.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A magneto-optical sensor for characterizing a free-space magnetic field, said magneto-optical sensor comprising:
    means for generating said free-space magnetic field, said means for generating comprising a pump and an emitter, said pump comprising a pulsed laser which outputs an optical pulse to said emitter, said emitter responding thereto by outputting said free-space magnetic field;
    a magneto-optic crystal positionable so that the free-space magnetic field passes therethrough, thereby changing an index of refraction thereof;
    means for generating an optical probe signal to impinge the magneto-optic crystal simultaneous with the free-space magnetic field passing therethrough;
    sensing means for determining ellipticity modulation of the optical probe signal after impinging upon the magneto-optic crystal; and
    means for characterizing the free-space magnetic field by evaluating the ellipticity modulation of the optical probe signal.

2. The magneto-optical sensor of claim 1, wherein said means for characterizing includes means for determining a change in the index of refraction of the magneto-optic crystal by analyzing the ellipiticity modulation of the optical probe signal.

3. The magneto-optical sensor of claim 1, wherein said optical probe signal generated by said means for generating said optical probe signal comprises a polarized optical probe signal.

4. The magneto-optical sensor of claim 1, wherein said free-space magnetic field comprises a terahertz beam, and wherein said optical probe signal comprises an optical pulse.

5. The magneto-optical sensor of claim 1, wherein said magneto-optic crystal comprises a terbium-gallium-garnet crystal.

6. The magneto-optical sensor of claim 1, wherein the free-space magnetic field comprises free-space electromagnetic radiation and wherein said means for characterizing includes means for determining both an amplitude and a phase of the free-space electromagnetic radiation from the ellipticity modulation of the optical probe signal.

7. The magneto-optical sensor of claim 1, wherein said means for generating said optical probe signal includes means for providing the optical probe signal to impinge the magneto-optic crystal parallel with an orientation of the magnetic field passing therethrough.

8. The magneto-optical sensor of claim 7, wherein the free-space magnetic field comprises a terahertz beam, and wherein said optical probe signal comprises a polarized optical probe signal.

9. Apparatus for characterizing magnetic components of free-space radiation, said apparatus comprising:
    means for generating said free-space radiation, said means for generating comprising a pump and an emitter, said pump comprising a pulsed laser which outputs an optical pulse to said emitter, said emitter responding thereto by outputting said free-space radiation;
    a magneto-optic crystal positionable so that at least a portion of the free-space radiation passes therethrough, said magneto-optic crystal having an index of refraction and a polarization changed by the free-space radiation passing therethrough in accordance with Faraday's effect;
    means for generating a polarized optical probe signal oriented to refract with said magneto-optic crystal simultaneous with said free space radiation passing therethrough, said optical probe signal optically sampling said change in the index of refraction and the polarization of the magneto-optic crystal; and
    means for processing said optical sample to characterize the magnetic components of the free-space radiation using the change in the index of refraction and the polarization of the magneto-optic crystal.

10. The apparatus of claim 9, wherein said means for processing comprises means for coherently quantifying both a phase of the free-space radiation and an amplitude of the free-space radiation using the change in the index of refraction and the polarization of the magneto-optic crystal.

11. The apparatus of claim 9, wherein the polarized optical probe signal passing through the magneto-optic crystal is substantially perpendicular to the direction of propagation of the free-space radiation passing through the magneto-optic crystal.

12. The apparatus of claim 9, wherein said means for generating comprises means for providing the optical probe signal to impinge the magneto-optic crystal parallel with the magnetic components of the free-space radiation passing therethrough.

13. The apparatus of claim 9, further comprising a lens positionable between the magneto-optic crystal and the source of free-space radiation, said lens focusing said free-space radiation within said magneto-optic crystal.

14. An imaging system for imaging an object, said imaging system comprising:
    means for generating a free-space radiation beam having a magnetic component, said free-space radiation beam being positionable to pass through the object to be imaged, said means for generating comprising a pump and an emitter, said pump comprising a pulsed laser which outputs an optical pulse to said emitter, said emitter responding thereto by outputting said free-space radiation beam;
    a magneto-optic crystal positionable so that the radiation beam passes through the magneto-optic crystal after passing through the object, said radiation beam changing the index of refraction of said magneto-optic crystal;
    means for generating an optical probe signal to impinge the magneto-optic crystal simultaneous with the radiation beam passing therethrough;
    sensing means for determining ellipticity modulation of the optical probe signal after impinging upon the magneto-optic crystal;

means for evaluating the ellipticity modulation of the optical probe signal to characterize the magnetic component of the radiation beam; and means for displaying an image of the said object using said characterization of said magnetic component of the radiation beam.

15. The imaging system of claim 14, wherein said magnetic radiation beam comprises a free-space terahertz beam.

16. The imaging system of claim 15, wherein said terahertz beam has a width at least equal to a width of the magneto-optic crystal.

17. The imaging system of claim 16, wherein the width of said terahertz beam is larger than the width of the magneto-optic crystal, and wherein the imaging system further comprises a lens device for focusing the terahertz beam into the magneto-optic crystal.

18. The imaging system of claim 14, wherein said means for evaluating further comprises means for coherently quantifying both a phase and an amplitude of the radiation beam passing through the magneto-optic crystal.

19. The imaging system of claim 14, wherein optical probe signal impinging upon the magneto-optic crystal is substantially perpendicular to a direction of propagation of the radiation beam passing through the magneto-optic crystal.

20. The imaging system of claim 14, wherein said means for generating the optical probe signal comprises means for providing the optical probe signal to impinge the magneto-optic crystal parallel with the magnetic component of the radiation beam passing therethrough.

\* \* \* \* \*

UNITED STATES PATENT AND TRADEMARK OFFICE
CERTIFICATE OF CORRECTION

PATENT NO. : 6,111,416
DATED : August 29, 2000
INVENTOR(S) : Zhang et al.

It is certified that error appears in the above-identified patent and that said Letters Patent is hereby corrected as shown below:

Title page,
Item [75] Inventors,
Line 1, delete "Jenifer" and replace with -- Jennifer --.

Signed and Sealed this

Ninth Day of October, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO.    : 6,111,416
DATED         : August 29, 2000
INVENTOR(S)   : Zhang et al.

Page 1 of 1

It is certified that error appears in the above-identified patent and that said Letters Patent is hereby corrected as shown below:

Column 1,
Line 6, please insert the following:

-- STATEMENT AS TO RIGHTS UNDER FEDERALLY SPONSORED RESEARCH

This invention was made with support from the Department of Energy under Grant No. DE-F607-98ER 62706. The United States government may have certain rights in the invention. --.

Signed and Sealed this

Thirteenth Day of September, 2005

JON W. DUDAS
*Director of the United States Patent and Trademark Office*